US012651643B2

(12) United States Patent
Zhou et al.

(10) Patent No.: US 12,651,643 B2
(45) Date of Patent: Jun. 9, 2026

(54) DETECTING SOMATIC SINGLE NUCLEOTIDE VARIANTS FROM CELL-FREE NUCLEIC ACID WITH APPLICATION TO MINIMAL RESIDUAL DISEASE MONITORING

(71) Applicant: THE REGENTS OF THE UNIVERSITY OF CALIFORNIA, Oakland, CA (US)

(72) Inventors: Xianghong Jasmine Zhou, Los Angeles, CA (US); Shuo Li, Los Angeles, CA (US); Wenyuan Li, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1354 days.

(21) Appl. No.: 16/647,339

(22) PCT Filed: Sep. 14, 2018

(86) PCT No.: PCT/US2018/051160
§ 371 (c)(1),
(2) Date: Mar. 13, 2020

(87) PCT Pub. No.: WO2019/055835
PCT Pub. Date: Mar. 21, 2019

(65) Prior Publication Data
US 2021/0125683 A1     Apr. 29, 2021

Related U.S. Application Data

(60) Provisional application No. 62/559,366, filed on Sep. 15, 2017.

(51) Int. Cl.
*G16B 20/20* (2019.01)
*G16B 40/20* (2019.01)

(52) U.S. Cl.
CPC ............. *G16B 20/20* (2019.02); *G16B 40/20* (2019.02)

(58) Field of Classification Search
CPC ....... G16B 20/20; G16B 40/20; C12Q 1/6886
See application file for complete search history.

(56) References Cited

U.S. PATENT DOCUMENTS

| | | | |
|---|---|---|---|
| 2014/0100121 A1 | 4/2014 | Lo et al. | |
| 2016/0032396 A1 | 2/2016 | Diehn et al. | |

FOREIGN PATENT DOCUMENTS

| | | |
|---|---|---|
| CN | 104662168 | 5/2015 |
| CN | 110914450 | 3/2020 |
| CN | 112820407 | 5/2021 |
| WO | WO 2016/141324 | 9/2016 |
| WO | WO 2017/106768 | 6/2017 |
| WO | WO-2017132661 A2 * | 8/2017 ........... A61K 31/519 |

OTHER PUBLICATIONS

Ben Lassoued, A. Minimal residual disease testing in hematulogic malignancies and solid cancer. Expert Review of Molecular Diagnostics 14(6): 699-712. (Year: 2014).*
Roberts, ND. A comparative analysis of algorithms for somatic SNV detection in cancer. Bioinformatics 29(18): 2223-2230. (Year: 2013).*
Spinella J-F. SNooPer: a machine learning-based method for somatic variant identification from low-pass next-generation sequencing. BMC Genomics 17(912): 1-11. (Year: 2016).*
Bareke et al. "Joint genotype inference with germline and somatic mutations." *BMC Bioinformatics* 2013, 14, pp. 1-11.
International Search Report and Written Opinion issued in corresponding application no. PCT/US2018/051160, dated Jan. 15, 2019.
Malhotra et al. "A frame-based representation of genomic sequences for removing errors and rare variant detection in NGS data." *arXiv*, 2016, pp. 1-13, Retrieved from the Internet:https://arxiv.org/pdf/1604.04803.pdf on Apr. 27, 2020.
Siravegna et al. "Integrating liquid biopsies into the management of cancer." *Nature Reviews: Clinical Oncology* 2017, 14 (9), pp. 531-548.
Cheng et al., "Next-generation sequencing (NGS) of tissue and cell free DNA (cfDNA) to identify somatic and germline alterations in advanced prostate cancer." Journal of Clinical Oncology 2017, 35(15) (Abstract only).
Search Report issued in corresponding Chinese Application No. 201880070782.2, dated Jul. 19, 2022.
Ziyang et al., *Study on High-Throughput Sequencing of Somatic Gene Mutations to Detect Reference Materials for Bioinformatics Analysis*. 2022. Chinese Excellent Doctoral and Master's Thesis Full-text Database (Doctor) Basic Sciences (No English translation provided).
Newman et al., "Integrated digital error suppression for improved detection of circulating tumor DNA" *Nature Biotechnology* 2016, 34(5), 547-555.
Partial Supplementary European Search Report issued in Corresponding European Application No. 18856959.4, dated May 20, 2021.

* cited by examiner

*Primary Examiner* — Olivia M. Wise
*Assistant Examiner* — Robert J. Kallal
(74) *Attorney, Agent, or Firm* — Norton Rose Fulbright US LLP

(57) ABSTRACT

The present disclosure provides a probabilistic model for accurate and sensitive somatic single nucleotide variant (SNV) detection in cell-free nucleic acid samples comprising a set of sequence data. A joint genotype may be determined for each locus in the set of sequence data, and germline mutations may be intrinsically removed. A set of filtrations can be applied to eliminate low quality somatic variant calls. Further, a global tumor cell-free deoxyribonucleic acid (cfDNA) fraction and overlapping read mates can be considered, thereby enabling accurate SNV detection and variant allele frequency estimation from samples with low tumor cfDNA fraction. A sensitive early detection of minimal residual disease (MRD) is designed by using the probabilistic model and the machine learning model for distinguishing true variants from sequencing errors.

17 Claims, 15 Drawing Sheets

Figure 1: Somatic mutations called from primary tumor sample, metastasis sample and/or cfDNA.

202

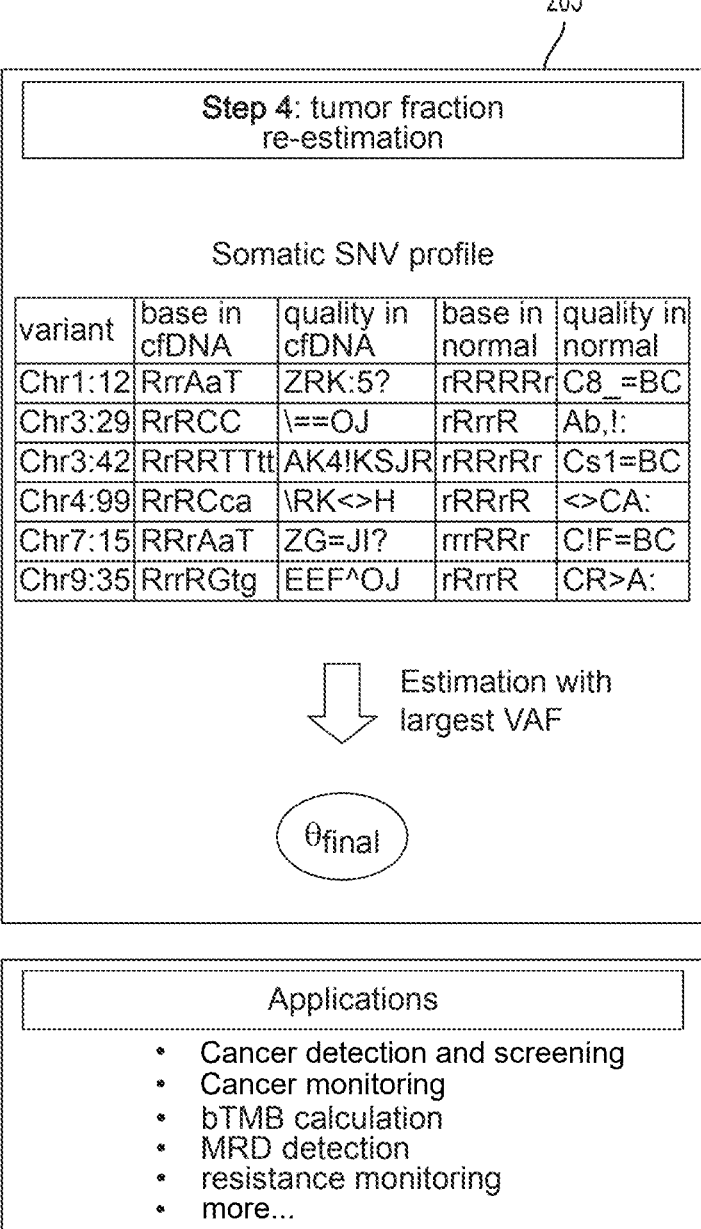

205

Step 4: tumor fraction re-estimation

Somatic SNV profile

| variant | base in cfDNA | quality in cfDNA | base in normal | quality in normal |
|---------|---------------|------------------|----------------|-------------------|
| Chr1:12 | RrrAaT | ZRK:5? | rRRRRr | C8_=BC |
| Chr3:29 | RrRCC | \==OJ | rRrrR | Ab,!: |
| Chr3:42 | RrRRTTtt | AK4!KSJR | rRRrRr | Cs1=BC |
| Chr4:99 | RrRCca | \RK<>H | rRRrR | <>CA: |
| Chr7:15 | RRrAaT | ZG=JI? | rrrRRr | C!F=BC |
| Chr9:35 | RrrRGtg | EEF^OJ | rRrrR | CR>A: |

⇩ Estimation with largest VAF

θfinal

Applications

- Cancer detection and screening
- Cancer monitoring
- bTMB calculation
- MRD detection
- resistance monitoring
- more...

Truncal somatic SNV profile at baseline

| variant | base in cfDNA | quality in cfDNA | base in normal | quality in normal |
|---------|---------------|------------------|----------------|-------------------|
| Chr1:12 | RrrAa*T* | ZRK:5? | rRRRRr | C8_=BC |
| Chr3:29 | RrRCC | \==OJ | rRrrR | Ab,!: |
| Chr3:42 | RrRR*TTtt* | AK4!KSJR | rRRrRr | Cs1=BC |
| Chr4:99 | RrRCca | \RK<>H | rRRrR | <>CA: |
| Chr7:15 | RRrAa*T* | ZG=JI? | rrrRRr | C!F=BC |
| Chr9:35 | RrrRGtg | EEF^OJ | rRrrR | CR>A: |

Filter errors with a ML model (readpair-based)

Plasma WES at T1

Filtered data

Calculate MRD index
using a within-sample
statistical test

MRD
index decision

900

DETECTING SOMATIC SINGLE NUCLEOTIDE VARIANTS FROM CELL-FREE NUCLEIC ACID WITH APPLICATION TO MINIMAL RESIDUAL DISEASE MONITORING

CROSS-REFERENCE TO RELATED APPLICATIONS

This application is a national phase application under 35 U.S.C. § 371 of International Application No. PCT/US2018/051160, filed Sep. 14, 2018, which claims the benefit of U.S. Provisional Patent Application No. 62/559,366, filed Sep. 15, 2017, each of which are expressly incorporated by reference herein in their entirety.

STATEMENT OF GOVERNMENT INTEREST

This invention was made with Government support under CA237711, HL108634, and CA246329 awarded by the National Institutes of Health. The government has certain rights in the invention.

BACKGROUND

Somatic mutations may accumulate in cells throughout a subject's lifetime. While the majority of such mutations may have little or no noticeable effect, some may alter genes and/or key cellular functions, and therefore produce a phenotype change. A product of somatic mutations may be cancer, which results from the clone expansion of cells and an escape from both the in-built programs of normal somatic cell behavior and the exogenous restraints on cell proliferation. Somatic mutations that trigger cancer progression may be referred to as "driver mutations," and somatic mutations that result in no phenotypic or biological consequences may be referred to as "passenger mutations."

Analyzing driver mutations, which may be commonly found in tumors, may be essential for analyzing cancer pathology, cancer diagnosis, precision oncology, and prognosis. Therefore, being able to obtain a genetic profile of a tumor may be important in both medical treatment and clinical research. According to some methods, a genetic profile of a tumor may be obtained from surgical or biopsy specimens. However, these procedures cannot always be performed because they may be costly, invasive, and can endanger the health of a subject or patient.

Notably, both somatic cells and tumors may release their nuclear and mitochondrial deoxyribonucleic acid (DNA) and/or ribonucleic acid (RNA) into a subject's bloodstream during cellular destruction (e.g., apoptosis and necrosis). As a result, genetic information of tumor cells can be found in a subject's bloodstream and extracted from plasma.

Recently, cell-free DNA (cfDNA) and cell-free RNA (cfRNA), which may be found in plasma, have been regarded as a biomarker of great potential in cancer diagnosis and prognosis. However, due to the mixed (e.g., containing both tumor and non-tumor) nature of cfDNA, detecting cancer-associated alleles from cfDNA sequencing data may be difficult. For example, specialized analysis may be required to detect tumor-derived DNA (ctDNA) and its mutation, because its quantity and quality in cfDNA can vary drastically. For instance, the fraction of ctDNA in cfDNA can range from 0.01% to 97%, while for early stage cancer the fraction may be generally below 10%. Because of the noninvasive nature of cfDNA, plasma samples can be easily and sequentially obtained for diagnosis and prognosis, thereby providing abundant information relating to cancer over a time period. Therefore, detecting cancer mutations in ctDNA may provide a promising protocol for early cancer diagnosis, monitoring, and minimal residual disease monitoring.

With respect to detecting single nucleotide variants (SNVs), or somatic mutations, many existing methods designed for impure solid tumor samples (such as, e.g., VarScan2 and MuTect) may not be easily used for samples with tumor fraction as low as cfDNA. Without considering special properties of cfDNA, such methods may not identify somatic SNVs even with strong evidence at low tumor fractions. In addition, methods developed to detect somatic SNVs in cfDNA include Capp-Seq with iDES and SiNVICT. Capp-Seq with iDES may refer to an experimental error-suppression technique based on the targeted sequencing panel, allowing for a sensitive detection of cancer mutations in blood cfDNA samples of subjects such as mid- to late-stage cancer patients. This method may address the low tumor fraction problem with deep sequencing to capture tumor signals in cfDNA. However, due to the expensive cost of deep sequencing, it can sequence only a small panel of genomic regions, thus limiting its detection power for different cancer types and application to personalized treatment and outcome prediction. SiNVICT may refer to a computational SNV caller, which uses a Poisson function to model the allelic distribution in cfDNA. This probabilistic model may be overly simplistic and may fail to consider the impure nature of cfDNA, resulting in a high number of false positives. Moreover, these methods may not consider overlapping read mates in cfDNA sequencing data, which can provide valuable information for detecting mutations in cfDNA.

SUMMARY

In view of the foregoing, the present disclosure provides a novel probabilistic method to detect somatic single nucleotide variants (SNVs) from cell-free deoxyribonucleic acid (cfDNA) or cell-free ribonucleic acid (cfRNA), which cannot only address unique challenges in cfDNA/cfRNA sequencing data. (e.g., low tumor fraction and low coverage of genome and high overlapping rate (for paired-end sequencing data)), but also estimate the tumor fraction in cfDNA/cfRNA (generally referred to as either cfDNA or cfRNA hereafter) for cancer diagnosis, prognosis, and minimal residual disease (MRD) detection after surgery. Specifically, the present disclosure provides methods for non-invasive cancer detection and diagnosis utilizing an examination of cfDNA. In doing so, methods and systems of the present disclosure may use a Bayesian-based probability framework to estimate the likelihood of a certain genotype from a set of sequencing data. Maximizing a posterior estimation may be used to determine a genotype of subjects (e.g., patients) and call somatic SNV candidates. Then somatic SNV candidates may be filtered with a set of criteria accommodating cfDNA properties, in terms of strand bias, variant qualities, sequence contexts, and known single nucleotide polymorphisms (SNPs). Further, both sequencing errors and low tumor variant allele frequencies in plasma samples may be taken into consideration. This approach may aid in the detection of somatic SNV and ensure good performance. This method may include one or more steps as detailed below.

According to an embodiment, a first step comprises estimating a tumor fraction by globally combining loci with variant alleles observed in sequencing data. The global tumor fraction estimation can effectively suppress sequencing noises and avoid the severe impact from sampling fluctuation and sequencing errors especially from low or medium depth sequencing. This cannot only improve accurate somatic SNV detection, but also may be a clinically valuable marker in cancer diagnosis and MRD detection by itself.

According to an embodiment, a second step comprises determining SNVs by maximizing a posterior of joint tumor-normal genotypes given the global tumor fraction. This approach may be in contrast to other approaches of comparing reads containing reference alleles and variant alleles.

According to an embodiment, a third step comprises utilizing a set of cfDNA-featured criteria, in terms of strand bias, variant qualities, sequence contexts, and known SNPs to filter somatic SNV candidates. Such post-call filtration ensures the high quality of variant calls in cfDNA.

According to an embodiment, a fourth step comprises re-estimating the somatic SNVs after filtration. This can be done using the global tumor fraction as described with respect to the first step.

Methods and systems of the present disclosure may be particular advantageous because (1) the global tumor fraction obtained in the first step may provide an expected level of tumor reads at individual locus even at low tumor fraction, such that somatic SNVs with low mutant frequency can still be distinguished from random sequencing errors; (2) the joint genotype model can better fit the cfDNA sequencing data with the presence of mixing normal and tumor-derived cfDNA, because it makes full use of both normal signals and tumor signals by simultaneously genotyping normal and tumor cfDNA; (3) computationally sequencing error suppression via a machine learning model can effectively distinguish true variants and sequencing errors based on the individual read information; and (4) the post-filtration of somatic SNV candidates may be particularly designed based on the cfDNA properties.

In view of these advantageous features, methods and systems of the present disclosure can be applied to not only deep targeted cfDNA sequencing data, but also medium-depth cfDNA sequencing data, such as whole exome sequencing data. Therefore, methods and systems of the present disclosure can offer sensitive mutation calls and mutational profile of cancer from cfDNA based on the input data.

As an example application of the inventive concepts, the mutational profile derived using methods and systems of the present disclosure can be used in early detection of Minimal Residual Disease (MRD) after surgery. The detection may be based on the known somatic mutation detected from matched tumor-normal samples from patients or from cfDNA in the plasma of patients before their surgeries. Truncal mutations for monitoring may be selected based on the mutation calling results from pairs. MRD may be determined by the statistically significant cumulative occurrence of the truncal mutations, as compared to the background in the follow-up plasma samples.

According to an aspect, the present disclosure provides a method for detecting somatic single nucleotide variants (SNVs) from cell-free nucleic acid, such as deoxyribo-nucleic acid (cfDNA) and ribonucleic acid (cfRNA), the method comprising: estimating, for a cfDNA sample comprising a set of sequence data, a global tumor cfDNA fraction; determining, for at least one locus k in the set of sequencing data, a genotype likelihood; eliminating, from the cfDNA sample comprising a set of sequence data, germline polymorphism; filtering SNV candidates by a set of filters; and analyzing, using a probabilistic model that incorporates the estimated global tumor cfDNA fraction, the cfDNA sample to determine a fraction of tumor-derived DNA (ctDNA) in the cfDNA sample.

In some embodiments, estimating, for the cfDNA sample, the global tumor cfDNA fraction comprises: combining information from all potential SNV sites in the cfDNA sample to reduce noise caused by a sequencing error occurring at one or more of the potential SNV sites. In some embodiments, determining the genotype likelihood comprises: calculating a likelihood of observing reads covering the locus given different joint genotypes. In some embodiments, determining the genotype likelihood comprises: estimating a genotype at a locus that maximizes a posterior probability. In some embodiments, estimating the genotype at the locus comprises: determining a joint genotype for each locus in the set of sequence data. In some embodiments, filtering the SNV candidates comprises at least one of: filtering SNV candidates based on a strand bias filter; filtering SNV candidates based on a base quality filter; filtering sequencing reads based on a read mate filter; filtering SNV candidates based on a read mate filter; and filtering sequencing reads based on a machine learning model that classifies true variants from sequencing errors. In some embodiments, filtering the sequencing reads based on the machine learning model that classifies true variants from sequencing errors, comprises: building ground-truth training data of sequencing reads that contain either true variants or sequencing errors; creating a feature profile of each sequencing read with information comprising sequencing quality of each base in the read, read alignment information, sequence context (such as read sequence and insertions/deletions), and insert size for paired-end sequencing data; training a classifier based on training data to classify sequencing reads having true variants and reads having sequencing errors, by using the feature profile of each read; and using the trained classifier to classify each cfDNA sequencing read as a read having true variants or a read having sequencing errors.

According to another aspect, the present disclosure provides a system for detecting somatic single nucleotide variants (SNVs) from cell-free nucleic acid, such as deoxy-ribonucleic acid (cfDNA) and ribonucleic acid (cfRNA), the system comprising: computer memory; one or more computer processors communicatively coupled to the computer memory, the one or more computer processors configured to implement a method comprising: estimating, for a cfDNA sample comprising a set of sequence data, a global tumor cfDNA fraction; determining, for at least one locus k in the set of sequencing data, a genotype likelihood; eliminating, from the cfDNA sample comprising a set of sequence data, germline polymorphism; filtering SNV candidates by a set of filters; and analyzing, using a probabilistic model that incorporates the estimated global tumor cfDNA fraction, the cfDNA sample to determine a fraction of tumor-derived DNA (ctDNA) in the cfDNA sample.

In some embodiments, estimating, for the cfDNA sample, the global tumor cfDNA fraction comprises: combining information from all potential SNV sites in the cfDNA sample to reduce noise caused by a sequencing error occurring at one or more of the potential SNV sites. In some embodiments, determining the genotype likelihood comprises: calculating a likelihood of observing reads covering the locus given different joint genotypes. In some embodiments, determining the genotype likelihood comprises: estimating a genotype at a locus that maximizes a posterior probability. In some embodiments, estimating the genotype at the locus comprises: determining a joint genotype for each locus in the set of sequence data. In some embodiments, filtering the SNV candidates comprises at least one of: filtering SNV candidates based on a strand bias filter; filtering SNV candidates based on a base quality filter; filtering sequencing reads based on a read mate filter; filtering SNV candidates based on a read mate filter; and filtering sequencing reads based on a machine learning model that classifies true variants from sequencing errors. In some embodiments, filtering the sequencing reads based on the machine learning model that classifies true variants from sequencing errors, comprises: building ground-truth training data of sequencing reads that contain either true variants or sequencing errors; creating a feature profile of each sequencing read with information comprising sequencing quality of each base in the read, read alignment information, sequence context (such as read sequence and insertions/deletions), and insert size for paired-end sequencing data; training a classifier based on training data to classify sequencing reads having true variants and reads having sequencing errors, by using the feature profile of each read; and using the trained classifier to classify each cfDNA sequencing read as a read containing having true variants or a read containing having sequencing errors.

According to another aspect, the present disclosure provides a method for detecting of minimal residual disease (MRD) from plasma samples, white blood cells, and resected tumor samples (if any), collected before and after surgery, the method comprising: identifying one or more truncal mutations and a mutation profile for each of the one or more truncal mutations from a pre-surgery blood sample and/or resected tumor sample; and detecting the MRD using follow-up plasma cfDNA samples after the surgery.

In some embodiments, detecting the MRD using the follow-up plasma cfDNA samples after the surgery, comprises: extracting reads that cover the position of truncal mutations, and using reads classified as having true variants to calculate an MRD predictive score. In some embodiments, using the reads classified as having true variants to calculate the MRD predictive score comprises: sampling k sites in a genome that do not include the identified mutations but match the characteristics of those k truncal mutations; filtering reads identified as comprising errors; and generating the MRD predictive score.

According to another aspect, the present disclosure provides a system for detecting of minimal residual disease (MRD) from plasma samples, white blood cells, and resected tumor samples (if any), collected before and after surgery, the system comprising: computer memory; one or more computer processors communicatively coupled to the computer memory, the one or more computer processors configured to implement a method comprising: identifying one or more truncal mutations and a mutation profile for each of the one or more truncal mutations from a pre-surgery blood sample and/or resected tumor sample; and detecting the MRD using follow-up plasma cfDNA samples after the surgery.

In some embodiments, detecting the MRD using the follow-up plasma cfDNA samples after the surgery, comprises: extracting reads that cover the position of truncal mutations and using reads classified as having true variants to calculate an MRD predictive score. In some embodiments, using the reads classified as having true variants to calculate the MRD predictive score comprises: sampling k sites in a genome that do not include the identified mutations but match the characteristics of those k truncal mutations; filtering reads identified as comprising errors; and generating the MRD predictive score.

According to another aspect, the present disclosure provides a system for detecting minimal residual disease (MRD) from plasma samples, white blood cells, and resected tumor samples (if any), collected before and after surgery, the system comprising: computer memory; one or more computer processors communicatively coupled to the computer memory, the one or more computer processors configured to implement a method comprising: identifying one or more truncal mutations and a mutation profile for each of the one or more truncal mutations from a pre-surgery blood sample and/or resected tumor sample; and detecting the MRD using follow-up plasma cfDNA samples after the surgery.

In some embodiments, detecting the MRD using the follow-up plasma cfDNA samples after the surgery, comprises: extracting reads that cover the position of truncal mutations and using reads classified as having true variants to calculate an MRD predictive score. In some embodiments, using the reads classified as having true variants to calculate the MRD predictive score comprises: sampling k sites in a genome that do not include the identified mutations but match the characteristics of those k truncal mutations; filtering reads identified as comprising errors; and generating the MRD predictive score.

According to another aspect, the present disclosure provides a non-transitory storage medium storing a set of instructions, that when executed, cause one or more computer processors to detect somatic single nucleotide variants (SNVs) from cell-free nucleic acid, such as deoxyribonucleic acid (cfDNA) and ribonucleic acid (cfRNA), the set of instructions comprising instructions to: for a cfDNA/cfRNA sample comprising a set of sequencing data, overlapping read mates, for the cfDNA/cfRNA sample comprising the set of sequence data, a global tumor cfDNA fraction; for a locus in the set of sequencing data, a genotype likelihood; eliminate, from the cfDNA/cfRNA sample comprising the set of sequence data, germline polymorphism; analyze, using a probabilistic model that incorporates the estimated global tumor cfDNA fraction, the cfDNA/cfRNA sample to determine a fraction of tumor-derived DNA (ctDNA/ctRNA) in the cfDNA/cfRNA sample; eliminate, using a set of filters that incorporate the properties of cfDNA/cfRNA sample, low-quality somatic SNV candidates; eliminate, from the cfDNA/cfRNA sample comprising the set of sequencing data, inconsistent overlapping read mates; eliminate, using a machine learning model that distinguishes sequencing errors from true variants, reads having sequencing errors; and determine, using a truncal mutational profile and the machine learning model, early minimal residual disease (MRD) from the cfDNA/cfRNA sample.

In some embodiments, estimating, for the cfDNA/cfRNA sample, the global tumor cfDNA fraction comprises: combining information from all potential SNV sites in the cfDNA/cfRNA sample to reduce noise caused by a sequencing error occurring at one or more of the potential SNV sites. In some embodiments, determining the genotype likelihood comprises: calculating a likelihood of observing reads covering the locus given different joint genotypes. In some embodiments, determining the genotype likelihood comprises: estimating a genotype at a locus that maximizes a posterior probability. In some embodiments, estimating the genotype at a locus comprises: determining a joint genotype for each locus in the set of sequence data. In some embodiments, eliminating the reads having sequencing errors comprises: training a machine learning model using samples sequenced multiple times; determining a base from true variants or sequencing errors in the set of sequencing data. In some embodiments, determining the early minimal residual disease (MRD) from the cfDNA/cfRNA sample comprises: determining truncal mutations from mutational profile and variant allele frequencies called from the cfDNA/ cfRNA sample; combining multiple variant loci to enhance tumor signal in ultra-low tumor fraction samples; and determining the MRD status by a within-sample statistical test.

According to another aspect, the present disclosure provides a method for detecting somatic single nucleotide variants (SNVs) from cell-free nucleic acid, such as deoxyribonucleic acid (cfDNA) and ribonucleic acid (cfRNA), the method comprising: merging, for a cfDNA/cfRNA sample comprising a set of sequencing data, overlapping read mates; estimating, for a cfDNA/cfRNA sample comprising the set of sequence data, a global tumor cfDNA fraction; determining, for a locus in the set of sequencing data, a genotype likelihood; eliminating, from the cfDNA/cfRNA sample comprising the set of sequence data, germline polymorphism; analyzing, using a probabilistic model that incorporates the estimated global tumor cfDNA fraction, the cfDNA/cfRNA sample to determine a fraction of tumor-derived DNA (ctDNA/ctRNA) in the cfDNA/cfRNA sample; eliminating, using a set of filters that incorporate the properties of cfDNA/cfRNA sample, low-quality somatic SNV candidates; eliminating, from the cfDNA/cfRNA sample comprising the set of sequencing data, inconsistent overlapping read mates; eliminating, using a machine learning model that distinguishes sequencing errors from true variants, reads having sequencing errors; and determining, using a truncal mutational profile and the machine learning model, early minimal residual disease (MRD) from the cfDNA/cfRNA sample.

In some embodiments, estimating, for the cfDNA/cfRNA sample, the global tumor cfDNA fraction comprises: combining information from all potential SNV sites in the cfDNA/cfRNA sample to reduce noise caused by a sequencing error occurring at one or more of the potential SNV sites. In some embodiments, determining the genotype likelihood comprises: calculating a likelihood of observing reads covering the locus given different joint genotypes. In some embodiments, determining the genotype likelihood comprises: estimating a genotype at a locus that maximizes a posterior probability. In some embodiments, estimating the genotype at a locus comprises: determining a joint genotype for each locus in the set of sequence data. In some embodiments, eliminating the reads having sequencing errors comprises: training a machine learning model using samples sequenced multiple times; determining a base from true variants or sequencing errors in the set of sequencing data. In some embodiments, determining the early minimal residual disease (MRD) from the cfDNA/cfRNA sample comprises: determining truncal mutations from mutational profile and variant allele frequencies called from the cfDNA/ cfRNA sample; combining multiple variant loci to enhance tumor signal in ultra-low tumor fraction samples; and determining the MRD status by a within-sample statistical test.

According to another aspect, the present disclosure provides a method for detecting somatic single nucleotide variants (SNVs) from a plurality of cell-free nucleic acid (cfNA) molecules of a subject, comprising: (a) retrieving a plurality of sequence reads generated by a sequencer wherein at least a subset of said plurality of sequence reads comprises sequences from said plurality of cfNA molecules or derivatives thereof; (b) applying a probabilistic model to said plurality of sequence reads at each of a plurality of genetic loci to estimate a global tumor burden of said plurality of cfNA molecules wherein said estimated global tumor burden comprises a quantitative measure of tumor-derived cfNA molecules among said plurality of cfNA molecules wherein said plurality of genetic loci comprises potential SNV sites; (c) determining, for each of said plurality of genetic loci, a likelihood of one or more genotypes of said subject based at least in part on said global tumor burden wherein said one or more genotypes are selected from the group consisting of a normal genotype, a tumor genotype, and a joint normal-tumor genotype; (d) for each of said plurality of genetic loci, detecting one or more SNVs, based at least in part on said likelihood of said one or more genotypes determined in (c) and said quantitative measure of tumor-derived cfNA molecules among said plurality of cfNA molecules; and (e) filtering out, from said one or more SNVs detected in (d), one or more germline polymorphisms, thereby obtaining one or more somatic SNVs.

In some embodiments, the method further comprises (f) filtering out said one or more somatic SNVs obtained in (e) using one or more filters selected from the group consisting of a strand bias filter, a base quality filter, a read mate filter, a sequencing error filter, an insertion or deletion (indel) and homopolymer induced error filter, and a public database filter, thereby obtaining a filtered set of somatic SNVs. In some embodiments, the method further comprises (g) applying said probabilistic model to said plurality of sequence reads at each of said plurality of genetic loci to re-estimate said global tumor burden wherein said plurality of genetic loci comprises said filtered set of somatic SNVs obtained in (f). In some embodiments, said plurality of cell-free nucleic acid (cfNA) molecules comprises cell-free deoxyribonucleic acid (cfDNA) molecules. In some embodiments, said plurality of cell-free nucleic acid (cfNA) molecules comprises cell-free ribonucleic acid (cfRNA) molecules. In some embodiments, estimating said global tumor burden comprises combining information from said plurality of sequence reads across said potential SNV sites to reduce noise in said plurality of sequence reads arising from errors in said sequencing at one or more of said potential SNV sites. In some embodiments, re-estimating said global tumor burden comprises combining information from said plurality of sequence reads across said filtered set of somatic SNVs to reduce noise in said plurality of sequence reads arising from errors in said sequencing at one or more of said filtered set of somatic SNVs. In some embodiments, combining said information comprises calculating an overall proportion of sequence reads among said plurality of sequence reads comprising an SNV among a plurality of predetermined SNV hotspots. In some embodiments, combining said information comprises calculating a value that maximizes a likelihood of observing said plurality of sequence reads at each of a plurality of predetermined SNV hotspots, given said global tumor burden. In some embodiments, combining said information comprises calculating a maximum of variant allele frequency values among a plurality of predetermined SNV hotspots. In some embodiments, said information comprises base calls, base qualities, mapping qualities, or a combination thereof. In some embodiments, determining said likelihood for said genetic locus comprises determining a likelihood of observing a number of sequence reads of said plurality of sequence reads covering said genetic locus, given the one or more genotypes. In some embodiments, determining said likelihood for said genetic locus comprises calculating a maximum a posteriori probability estimate. In some embodiments, determining said likelihood for said genetic locus comprises determining a joint normal-tumor genotype for said genetic locus. In some embodiments, said filtering is performed using one or more filters selected from the group consisting of strand bias filter, base quality filter, read mate filter, sequence context filter, and sequencing error filter. In some embodiments, said probabilistic model comprises a machine learning model configured to classify sequence reads having true variants from sequence reads having sequencing errors.

In some embodiments, the method further comprises subjecting said plurality of cfNA molecules to amplification. In some embodiments, said amplification comprises polymerase chain reaction (PCR). In some embodiments, the method further comprises processing said detected somatic SNVs against a reference. In some embodiments, said reference comprises a second set of somatic SNVs detected from a plurality of cfNA molecules of one or more additional subjects. In some embodiments, said plurality of cfNA molecules is obtained from a bodily sample of said subject. In some embodiments, said bodily sample is selected from the group consisting of plasma, serum, bone marrow, cerebral spinal fluid, pleural fluid, saliva, stool, and urine. In some embodiments, the method further comprises processing said detected somatic SNVs to generate a likelihood of said subject as having or being suspected of having a disease or disorder. In some embodiments, said disease or disorder is a cancer selected from the group consisting of pancreatic cancer, liver cancer, lung cancer, colorectal cancer, leukemia, bladder cancer, bone cancer, brain cancer, breast cancer, cervical cancer, endometrial cancer, esophageal cancer, gastric cancer, head and neck cancer, melanoma, ovarian cancer, testicular cancer, kidney cancer, sarcoma, bile duct cancer, and prostate cancer. In some embodiments, the method further comprises sequencing said plurality of cfNA molecules or derivatives thereof to yield said plurality of sequence reads. In some embodiments, said somatic SNVs comprise cancer driver mutations.

According to another aspect, the present disclosure provides a system for detecting somatic single nucleotide variants (SNVs) from a plurality of cell-free nucleic acid (cfNA) molecules of a subject, comprising: a database storing a plurality of sequence reads wherein at least a subset of said plurality of sequence reads comprises sequences from said plurality of cfNA molecules or derivatives thereof; and one or more computer processors operatively coupled to said database wherein said one or more computer processors are individually or collectively programmed to: (1) retrieve said plurality of sequence reads from said database; (2) apply a probabilistic model to said plurality of sequence reads at each of a plurality of genetic loci to estimate a global tumor burden of said plurality of cfNA molecules wherein said estimated global tumor burden comprises a quantitative measure of tumor-derived cfNA molecules among said plurality of cfNA molecules wherein said plurality of genetic loci comprises potential SNV sites; (3) determine, for each of said plurality of genetic loci, a likelihood of one or more genotypes of said subject based at least in part on said global tumor burden wherein said one or more genotypes are selected from the group consisting of a normal genotype, a tumor genotype, and a joint normal-tumor genotype; (4) for each of said plurality of genetic loci, detect one or more SNVs, based at least in part on said likelihood of said one or more genotypes determined in (3) and said quantitative measure of tumor-derived cfNA molecules among said plurality of cfNA molecules; and (5) filter out, from said one or more SNVs detected in (4), one or more germline polymorphisms, thereby obtaining one or more somatic SNVs.

In some embodiments, said one or more computer processors are individually or collectively programmed to further (6) filter out said one or more somatic SNVs obtained in (5) using one or more filters selected from the group consisting of a strand bias filter, a base quality filter, a read mate filter, a sequencing error filter, an insertion or deletion (indel) and homopolymer induced error filter, and a public database filter, thereby obtaining a filtered set of somatic SNVs. In some embodiments, said one or more computer processors are individually or collectively programmed to further (7) apply said probabilistic model to said plurality of sequence reads at each of said plurality of genetic loci to re-estimate said global tumor burden wherein said plurality of genetic loci comprises said filtered set of somatic SNVs obtained in (6). In some embodiments, said plurality of cell-free nucleic acid (cfNA) molecules comprises cell-free deoxyribonucleic acid (cfDNA) molecules. In some embodiments, said plurality of cell-free nucleic acid (cfNA) molecules comprises cell-free ribonucleic acid (cfRNA) molecules. In some embodiments, estimating said global tumor burden comprises combining information from said plurality of sequence reads across said potential SNV sites to reduce noise in said plurality of sequence reads arising from errors in said sequencing at one or more of said potential SNV sites. In some embodiments, re-estimating said global tumor burden comprises combining information from said plurality of sequence reads across said filtered set of somatic SNVs to reduce noise in said plurality of sequence reads arising from errors in said sequencing at one or more of said filtered set of somatic SNVs. In some embodiments, combining said information comprises calculating an overall proportion of sequence reads among said plurality of sequence reads comprising an SNV among a plurality of predetermined SNV hotspots. In some embodiments, combining said information comprises calculating a value that maximizes a likelihood of observing said plurality of sequence reads at each of a plurality of predetermined SNV hotspots, given said global tumor burden. In some embodiments, combining said information comprises calculating a maximum of variant allele frequency values among a plurality of predetermined SNV hotspots. In some embodiments, said information comprises base calls, base qualities, mapping qualities, or a combination thereof. In some embodiments, determining said likelihood for said genetic locus comprises determining a likelihood of observing a number of sequence reads of said plurality of sequence reads covering said genetic locus, given the one or more genotypes. In some embodiments, determining said likelihood for said genetic locus comprises calculating a maximum a posteriori probability estimate. In some embodiments, determining said likelihood for said genetic locus comprises determining a joint normal-tumor genotype for said genetic locus. In some embodiments, said filtering is performed using one or more filters selected from the group consisting of strand bias filter, base quality filter, read mate filter, sequence context filter, and sequencing error filter. In some embodiments, said probabilistic model comprises a machine learning model configured to classify sequence reads having true variants from sequence reads having sequencing errors.

In some embodiments, said one or more computer processors are individually or collectively programmed to process said detected somatic SNVs against a reference. In some embodiments, said reference comprises a second set of somatic SNVs detected from a plurality of cfNA molecules of one or more additional subjects. In some embodiments, said plurality of cfNA molecules is obtained from a bodily sample of said subject. In some embodiments, said bodily sample is selected from the group consisting of plasma, serum, bone marrow, cerebral spinal fluid, pleural fluid, saliva, stool, and urine. In some embodiments, said one or more computer processors are individually or collectively programmed to process said detected somatic SNVs to generate a likelihood of said subject as having or being suspected of having a disease or disorder. In some embodiments, said disease or disorder is a cancer selected from the group consisting of pancreatic cancer, liver cancer, lung cancer, colorectal cancer, leukemia, bladder cancer, bone cancer, brain cancer, breast cancer, cervical cancer, endometrial cancer, esophageal cancer, gastric cancer, head and neck cancer, melanoma, ovarian cancer, testicular cancer, kidney cancer, sarcoma, bile duct cancer, and prostate cancer. In some embodiments, said somatic SNVs comprise cancer driver mutations.

According to another aspect, the present disclosure provides a non-transitory computer-readable medium comprising machine executable code that, upon execution by one or more computer processors, implements a method for detecting somatic single nucleotide variants (SNVs) from a plurality of cell-free nucleic acid (cfNA) molecules of a subject, said method comprising: (a) retrieving a plurality of sequence reads generated by a sequencer wherein at least a subset of said plurality of sequence reads comprises sequences from said plurality of cfNA molecules or derivatives thereof; (b) applying a probabilistic model to said plurality of sequence reads at each of a plurality of genetic loci to estimate a global tumor burden of said plurality of cfNA molecules wherein said estimated global tumor burden comprises a quantitative measure of tumor-derived cfNA molecules among said plurality of cfNA molecules wherein said plurality of genetic loci comprises potential SNV sites; (c) determining, for each of said plurality of genetic loci, a likelihood of one or more genotypes of said subject based at least in part on said global tumor burden wherein said one or more genotypes are selected from the group consisting of a normal genotype, a tumor genotype, and a joint normal-tumor genotype; (d) for each of said plurality of genetic loci, detecting one or more SNVs, based at least in part on said likelihood of said one or more genotypes determined in (c) and said quantitative measure of tumor-derived cfNA molecules among said plurality of cfNA molecules; and (e) filtering out, from said one or more SNVs detected in (d), one or more germline polymorphisms, thereby obtaining one or more somatic SNVs.

In some embodiments, the method further comprises (f) filtering out said one or more somatic SNVs obtained in (e) using one or more filters selected from the group consisting of a strand bias filter, a base quality filter, a read mate filter, a sequencing error filter, an insertion or deletion (indel) and homopolymer induced error filter, and a public database filter, thereby obtaining a filtered set of somatic SNVs. In some embodiments, the method further comprises (g) applying said probabilistic model to said plurality of sequence reads at each of said plurality of genetic loci to re-estimate said global tumor burden wherein said plurality of genetic loci comprises said filtered set of somatic SNVs obtained in (f). In some embodiments, said plurality of cell-free nucleic acid (cfNA) molecules comprises cell-free deoxyribonucleic acid (cfDNA) molecules. In some embodiments, said plurality of cell-free nucleic acid (cfNA) molecules comprises cell-free ribonucleic acid (cfRNA) molecules. In some embodiments, estimating said global tumor burden comprises combining information from said plurality of sequence reads across said potential SNV sites to reduce noise in said plurality of sequence reads arising from errors in said sequencing at one or more of said potential SNV sites. In some embodiments, re-estimating said global tumor burden comprises combining information from said plurality of sequence reads across said filtered set of somatic SNVs to reduce noise in said plurality of sequence reads arising from errors in said sequencing at one or more of said filtered set of somatic SNVs. In some embodiments, combining said information comprises calculating an overall proportion of sequence reads among said plurality of sequence reads comprising an SNV among a plurality of predetermined SNV hotspots. In some embodiments, combining said information comprises calculating a value that maximizes a likelihood of observing said plurality of sequence reads at each of a plurality of predetermined SNV hotspots, given said global tumor burden. In some embodiments, combining said information comprises calculating a maximum of variant allele frequency values among a plurality of predetermined SNV hotspots. In some embodiments, said information comprises base calls, base qualities, mapping qualities, or a combination thereof. In some embodiments, determining said likelihood for said genetic locus comprises determining a likelihood of observing a number of sequence reads of said plurality of sequence reads covering said genetic locus, given the one or more genotypes. In some embodiments, determining said likelihood for said genetic locus comprises calculating a maximum a posteriori probability estimate. In some embodiments, determining said likelihood for said genetic locus comprises determining a joint normal-tumor genotype for said genetic locus. In some embodiments, said filtering is performed using one or more filters selected from the group consisting of strand bias filter, base quality filter, read mate filter, sequence context filter, and sequencing error filter. In some embodiments, said probabilistic model comprises a machine learning model configured to classify sequence reads having true variants from sequence reads having sequencing errors.

In some embodiments, said method further comprises processing said detected somatic SNVs against a reference. In some embodiments, said reference comprises a second set of somatic SNVs detected from a plurality of cfNA molecules of one or more additional subjects. In some embodiments, said plurality of cfNA molecules is obtained from a bodily sample of said subject. In some embodiments, said bodily sample is selected from the group consisting of plasma, serum, bone marrow, cerebral spinal fluid, pleural fluid, saliva, stool, and urine. In some embodiments, said method further comprises processing said detected somatic SNVs to generate a likelihood of said subject as having or being suspected of having a disease or disorder. In some embodiments, said disease or disorder is a cancer selected from the group consisting of pancreatic cancer, liver cancer, lung cancer, colorectal cancer, leukemia, bladder cancer, bone cancer, brain cancer, breast cancer, cervical cancer, endometrial cancer, esophageal cancer, gastric cancer, head and neck cancer, melanoma, ovarian cancer, testicular cancer, kidney cancer, sarcoma, bile duct cancer, and prostate cancer. In some embodiments, said somatic SNVs comprise cancer driver mutations.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present disclosure, reference is now made to the following descriptions taken in conjunction with the accompanying figures, in which:

FIGS. 2A-2E illustrate a flowchart of a method for detecting single nucleotide variants (SNVs) from plasma cell-free deoxyribonucleic acid (cfDNA) according to an embodiment;

DETAILED DESCRIPTION OF THE INVENTION

Figure 1:
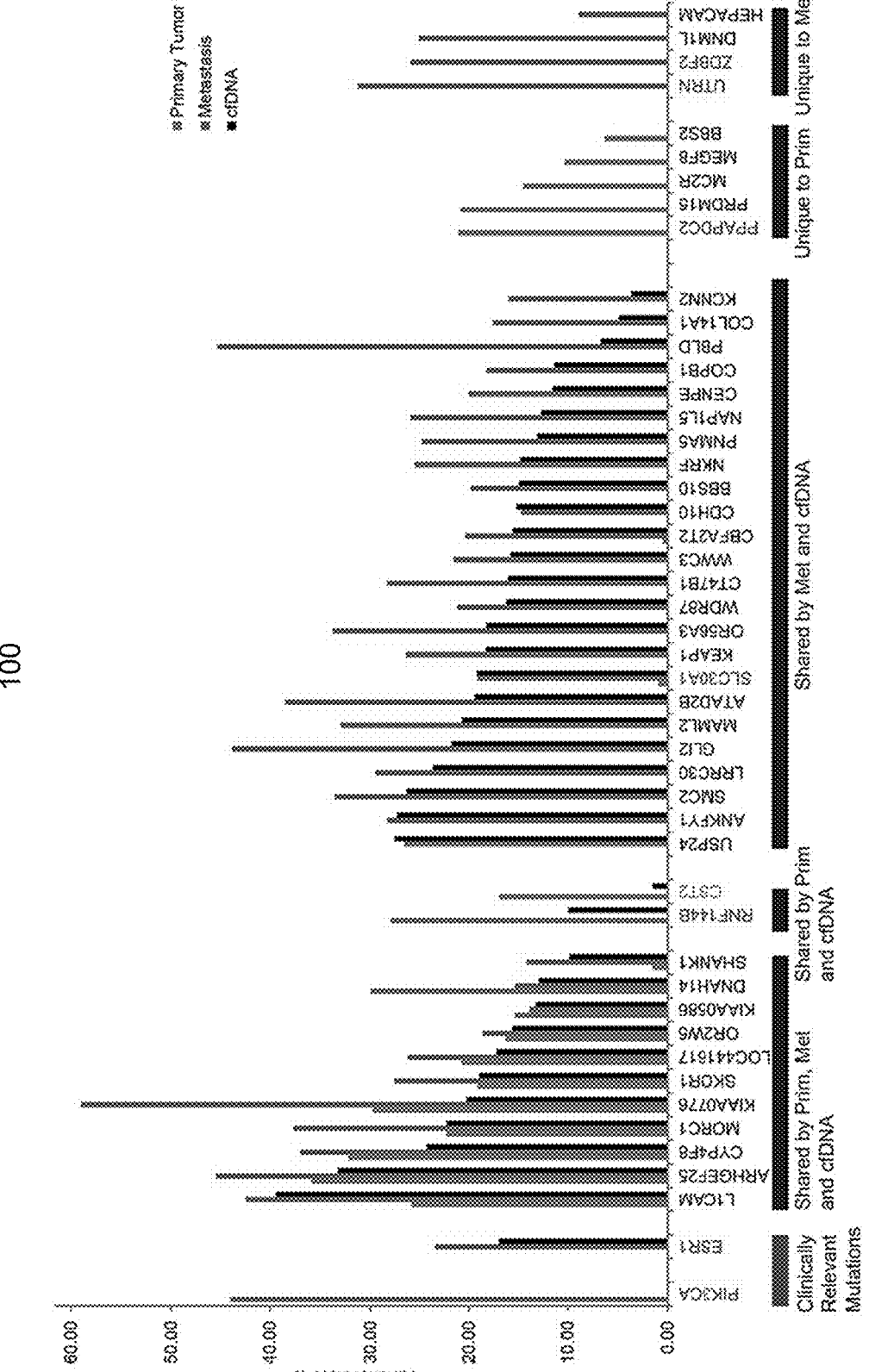
FIG. 1 illustrates a panel of a set of variant genes and their variant frequencies in different sample types according to an embodiment.
Figure 2A:
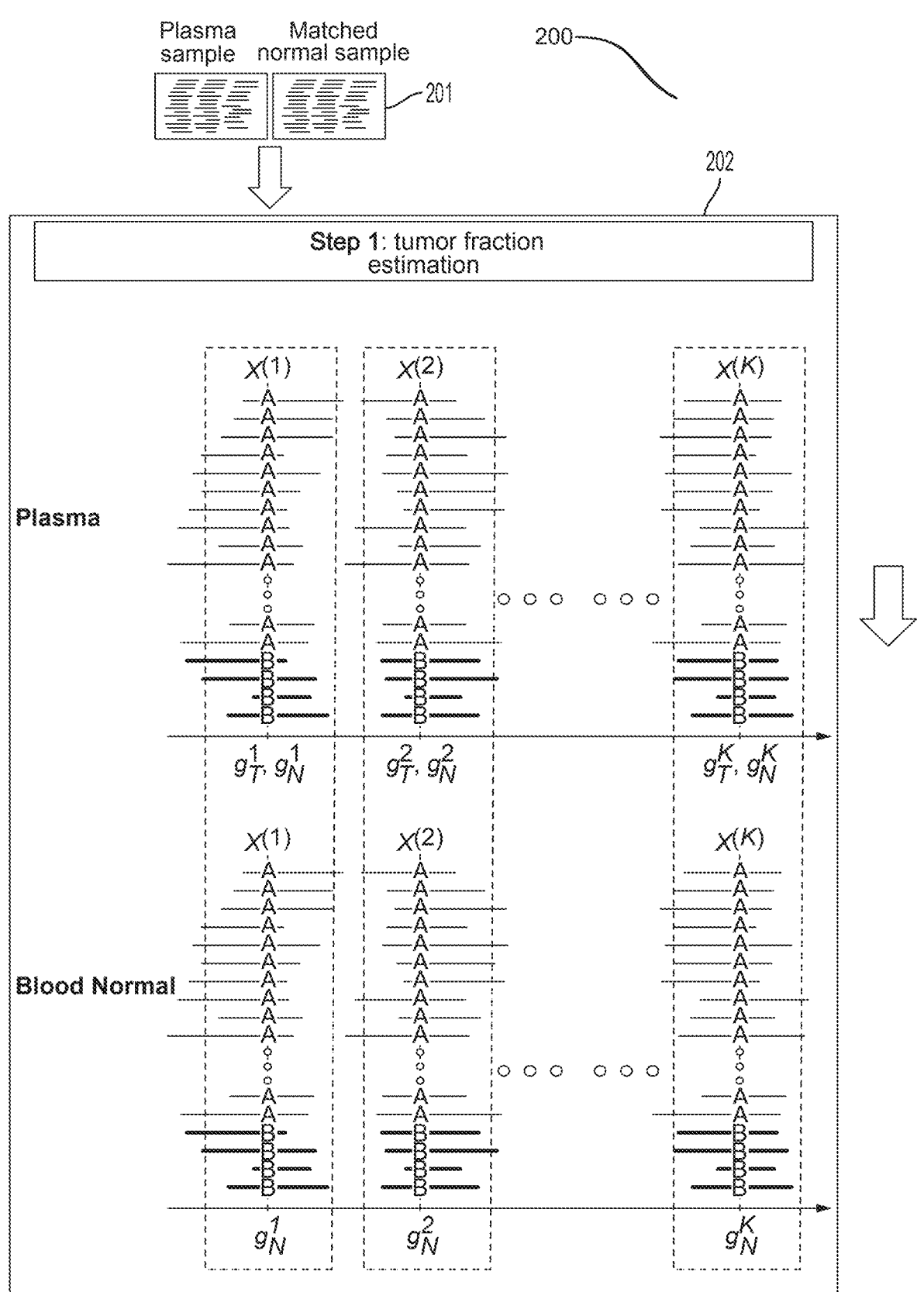
Figure 2B:
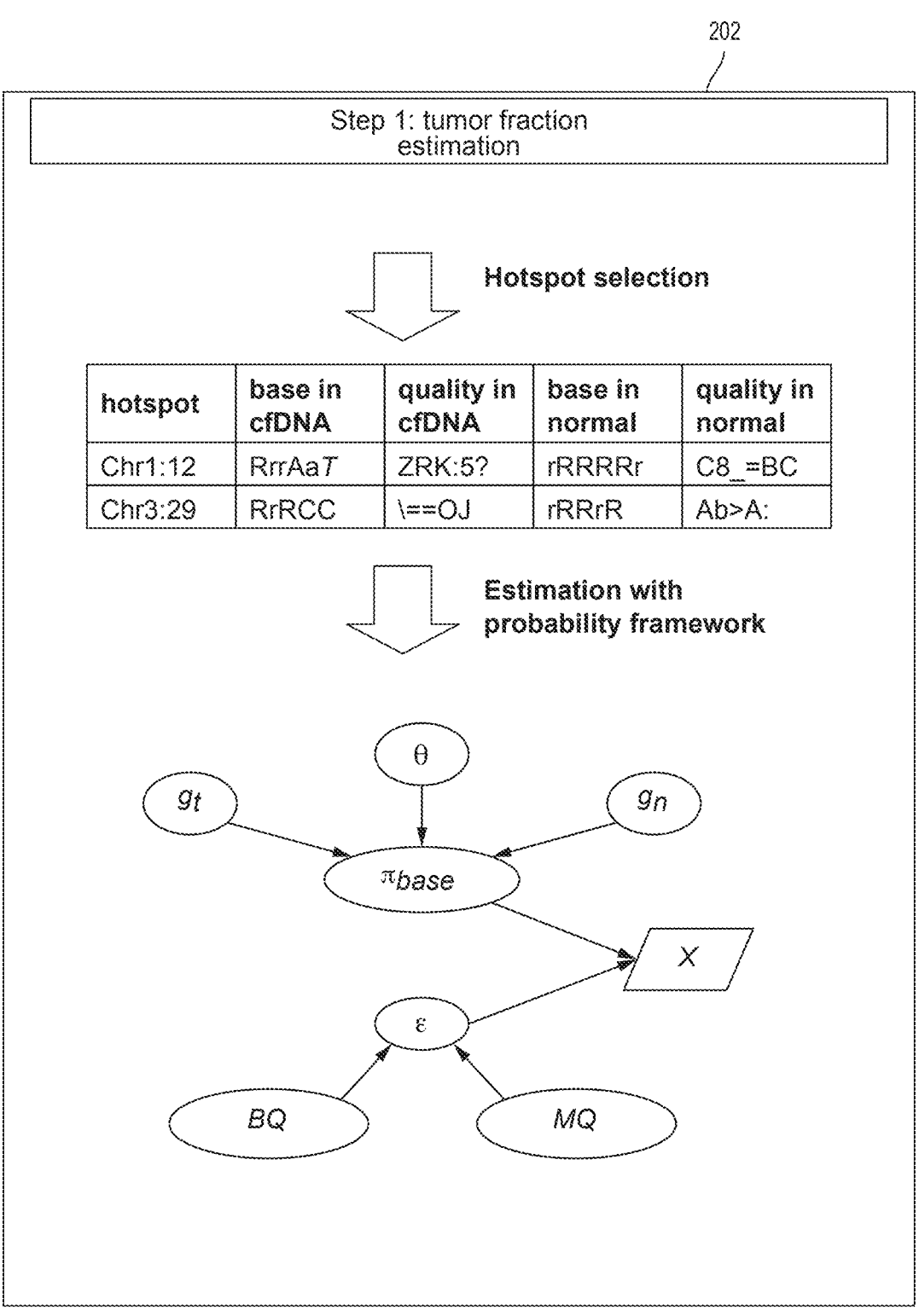
Figure 2C:
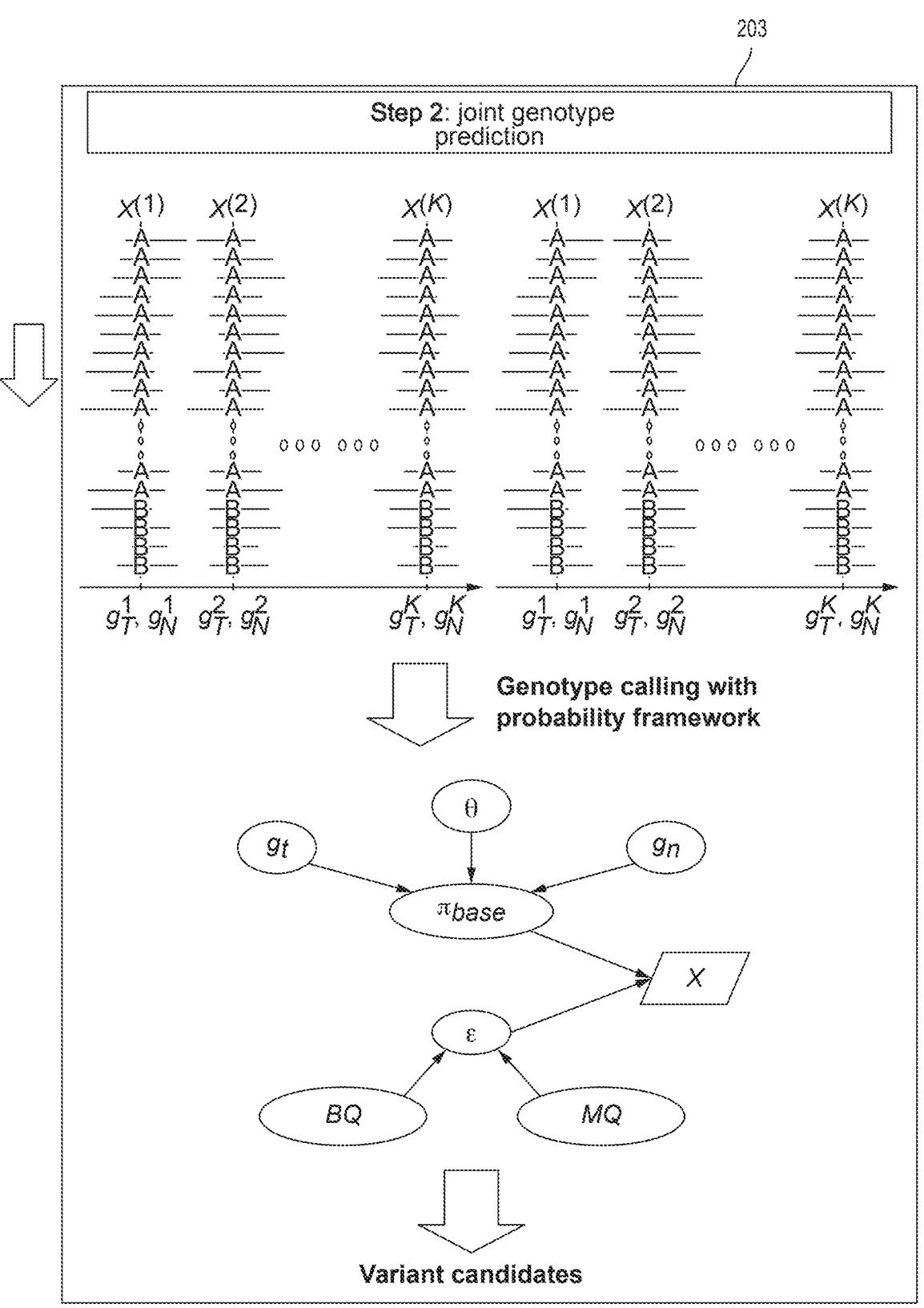
Figure 2D:
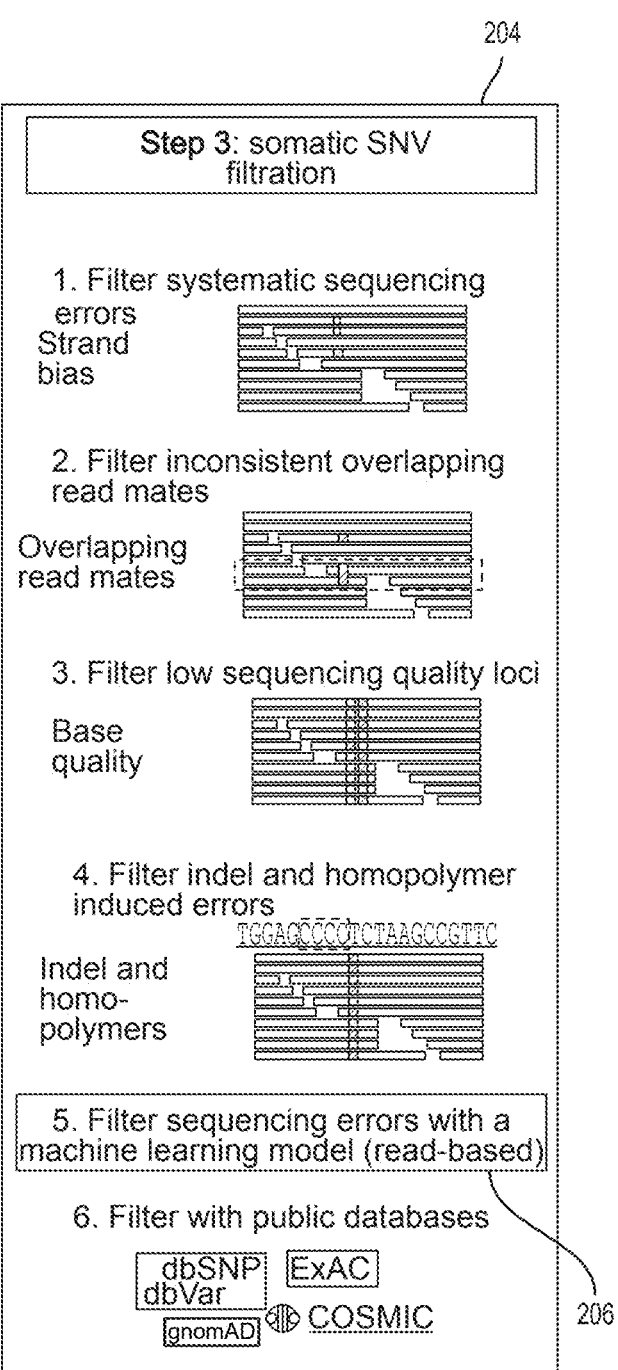

The present disclosure provides a probabilistic model for accurate and sensitive somatic single nucleotide variant (SNV) detection in cell-free deoxyribonucleic acid (cfDNA) and/or cell-free ribonucleic acid (cfRNA) samples comprising a set of sequence data. The cfDNA samples can be taken from plasma samples. This model may receive sequencing data from cfDNA and matched normal sample (e.g. from white blood cells in the blood) as input. Further, since a joint genotype may be determined for each locus in the set of sequence data, germline mutations may be removed. In addition, because a global tumor cfDNA fraction may be considered, accurate SNV detection can be performed from samples with low tumor fraction, which may not be available with other approaches.

As discussed herein, cfDNA from subjects (e.g., cancer patients) may comprise a mixture of DNA or RNA from cells of diseased organs (e.g., tumor cells) and DNA or RNA from normal cells. Therefore, the genotype of cfDNA can be modeled as a normal-tumor joint genotype. For a given locus, a prior variant allele frequency (prior VAF) of tumor genotype, denoted as 0, can be approximated as the fraction of mutated reads. (e.g. tumor cfDNA fraction). The tumor cfDNA fraction in early cancer patients may be often below 10%, so to accurately estimate somatic SNVs in tumor cells, the tumor cfDNA fraction may be estimated first. It may be assumed that tumor cfDNA fraction is uniform across the genome in a single sample.

Methods and systems of the present disclosure may maximize the likelihood of observing the sequencing reads, $P(X|\theta)$, to estimate the tumor cfDNA fraction, or to use the mean of variant allele frequencies of predefined, frequently observed variants in cancer. Since the tumor cfDNA fraction may be assumed to be uniform, data from hotspots can be utilized to estimate the tumor cfDNA fraction. According to an embodiment, hotspots can be selected using the following criteria: (1) the major allele may be the reference base; (2) the locus in the matched normal sample may be homozygous and may be the same as the reference; (3) the sequencing error probability of the reads supporting minor alleles may be less than the observed frequency of the allele; (4) at least one read with variant alleles may be observed; and (5) reads covering the locus must pass strand bias filters. Hence, sequencing noise may be eliminated. The probability of observing a read or a base can be calculated with the mapping quality of the read (which is the probability of misalignment) and the base quality of the sequenced bases (which is the probability of sequencing error). To determine the genotype of a locus, a likelihood of observing reads covering the locus given different joint genotypes may be calculated.

According to an embodiment, the posterior probability of a joint genotype is calculated from the set of sequence data. The joint genotype with the maximum posterior probability may be regarded as the true genotype at a given locus. Post-filtrations can be applied to detected somatic variants, which can rule out loci with strand bias, low coverage, or in tandem repeats. A final tumor fraction may be estimated as the maximum variant allele frequency of somatic variants passed filtrations.

Input data may comprise raw sequencing reads of cfDNA from subjects (e.g., patients). Also, embodiments can provide a somatic SNV report after analysis. When detecting SNVs from cfDNA, embodiments may accept a panel, where loci having the highest probability of containing tumor-derived point mutations are evaluated. For example, FIG. 1 shows panel 100, which can be obtained by analyzing public cancer databases or collecting known mutations in published literature.

A primary challenge of detecting SNVs from cfDNA may be the low fraction of tumor-derived cfDNA in the blood stream, which makes it difficult to differentiate mutations from sequencing errors. Without having special concern for the tumor cfDNA fraction, it may be unreliable to detect mutations. Methods and systems of the present disclosure may address challenge by incorporating the low tumor cfDNA fraction into a probability framework, e.g., explicitly considering the low fraction of tumor-derived cfDNA. To that end, a global tumor cfDNA fraction θ may be estimated by combining information from all potential SNV sites, and particularly sites known to drive mutations. Combining sites in this way may eliminate noise caused by sequencing errors at a single site. The estimated $\theta$ may then be utilized to accurately call SNV at individual sites. In some examples, an SNV at individual sites may be called at an accuracy of at least 80%, 90%, 95%, 96%, 97%, 98%, 99%, or more.

FIGS. 2A-2E illustrate a generalized flowchart of method 200 for detecting SNVs from plasma cfDNA according to a disclosed embodiment. According to method 200, raw sequencing data 201 may include a plasma cfDNA sample and a matched normal sample (such as white blood cells from the same subject) and may be input to block 202. Raw sequencing data 201 can comprise input files such as alignment files (.sam files or .bam files) and pileup files (.pileup files). Data in regions along a panel, such as panel 100 illustrated in FIG. 1, is extracted from raw sequencing files 201.

Raw sequencing data may be obtained from sequencing the plasma cfDNA sample or derivative thereof (e.g., an amplified or enriched product). Sequencing methods may include, but are not limited to, high-throughput sequencing, pyrosequencing, sequencing-by-synthesis, single-molecule sequencing, nanopore sequencing, semiconductor-based sequencing, sequencing-by-ligation, sequencing-by-hybridization, RNA-Seq (e.g., Illumina), Digital Gene Expression (Helicos), Next generation sequencing (e.g., Illumina, Pacific Biosciences of California, Ion Torrent), Single Molecule Sequencing by Synthesis (SMSS) (e.g., Helicos), massively-parallel sequencing, Clonal Single Molecule Array (e.g., Solexa), shotgun sequencing, Maxim-Gilbert sequencing, and primer walking.

Raw sequencing data may be preprocessed to improve mapping quality. Those reads with low quality mappings may be recalibrated and locally realigned based on the reference genome. Bases with low base qualities can also be eliminated by setting a hard threshold, which can ensure a low sequencing error rate.

Tumor cfDNA fraction estimation block 202 may estimate a global tumor cfDNA fraction using the preprocessed sequencing data, which includes information extracted from SAM or BAM files and/or PILEUP files. That is, at step 202, tumor fraction estimation is performed by globally combining loci with variant alleles observed in sequencing data. The global tumor fraction estimation can effectively suppress sequencing noises and avoid the severe impact from sampling fluctuation and sequencing errors especially from low or medium depth sequencing. It can not only improve accurate somatic SNV detection, but also may be a clinically valuable marker in cancer diagnosis and MRD detection by itself.

Step 203 may comprise determining SNVs by maximizing a posterior of joint tumor-normal genotypes given the global tumor fraction. This may be in contrast to other approaches of comparing reads containing reference alleles and variant alleles.

Step 204 may comprise using a set of cfDNA-featured criteria, in terms of strand bias, variant qualities, sequence contexts, and known SNPs, to filter somatic SNV candidates.

Such post-call filtration may ensure the high quality of variant calls in cfDNA.

Step 205 may comprise re-estimating the somatic SNVs after filtration. This can be done using the global tumor fraction as described with respect to the first step. At block 205, in examining the cfDNA sample and its matched normal sample, variant allele frequencies may be given special consideration. For instance, the variant allele frequency may not be treated simply as 0.5 for heterozygous variants and 1.0 for homozygous variants, since the actual variant allele frequency may be closely related to the amount of tumor-derived cfDNA present in the blood stream. This approach may represent an improvement over other SNV detection approaches.

Traditional SNV methods may assume that all observed alleles are from diploid chromosomes, where the first chromosome copy holds genotype $g_1$ and the second chromosome copy holds $g_2$. The biallelic genotype at a locus may therefore be represented by a couplet $G=(g_1, g_2)$, where the prior allele frequencies of $g_1$ and $g_2$ are 50% and 50%. This abstraction may assume that a tumor sample under examination is pure or nearly pure (e.g., the tumor genotypes dominate the sample). However, as discussed herein, methods and systems of the present disclosure may account for the fact that cfDNA may actually comprise a mixture of tumor-derived DNA and non-tumor-derived DNA. Accordingly, such approaches may focus only on the loci without germline polymorphism, and model cfDNA's genotype as $G=(g_n, g_t)$, where $g_n=(g_{n_1}, g_{n_2})$ is the genotype from normal cfDNA and $g_t=(g_{t_1}, g_{t_2})$ is the genotype from tumor-derived cfDNA. For a particular locus, the prior variant allele frequency (prior VAF) of $g_t$, denoted as $\theta$, can be approximated as the fraction of mutated reads, or tumor cfDNA fraction. Then $(1-\theta)$ is the prior frequency of $g_n$. However, given a very low proportion of tumor-derived cfDNA, such an approximation of $\theta$ at a single locus may be highly noisy. To address such challenges, an assumption may be made that an entire sample shares the same prior allele frequency, and therefore, operates using a global tumor cfDNA fraction (e.g., a global $\theta$).

The method illustrated in FIGS. 2A-2E may be advantageous because (1) the global tumor fraction obtained in the first step may yield an expected level of tumor reads at individual locus even at low tumor fraction, such that somatic SNVs with low mutant frequency can still be distinguished from random sequencing errors; (2) the joint genotype model can better fit the cfDNA sequencing data with the presence of mixing normal and tumor-derived cfDNA, by making full use of both normal signals and tumor signals by simultaneously genotyping normal and tumor cfDNA; (3) computationally sequencing error suppression via a machine learning model can effectively distinguish true variants and sequencing errors based on the individual read information; and (4) the post-filtration of somatic SNV candidates can be particularly designed based on the cfDNA properties. In view of these advantageous features, methods and systems of the present disclosure can be applied to not only deep targeted cfDNA sequencing data, but also medium-depth cfDNA sequencing data, such as whole exome sequencing data. Therefore, methods and systems of the present disclosure can offer sensitive mutation calls and mutational profile of cancer from cfDNA based on the input data.

Figure 3:
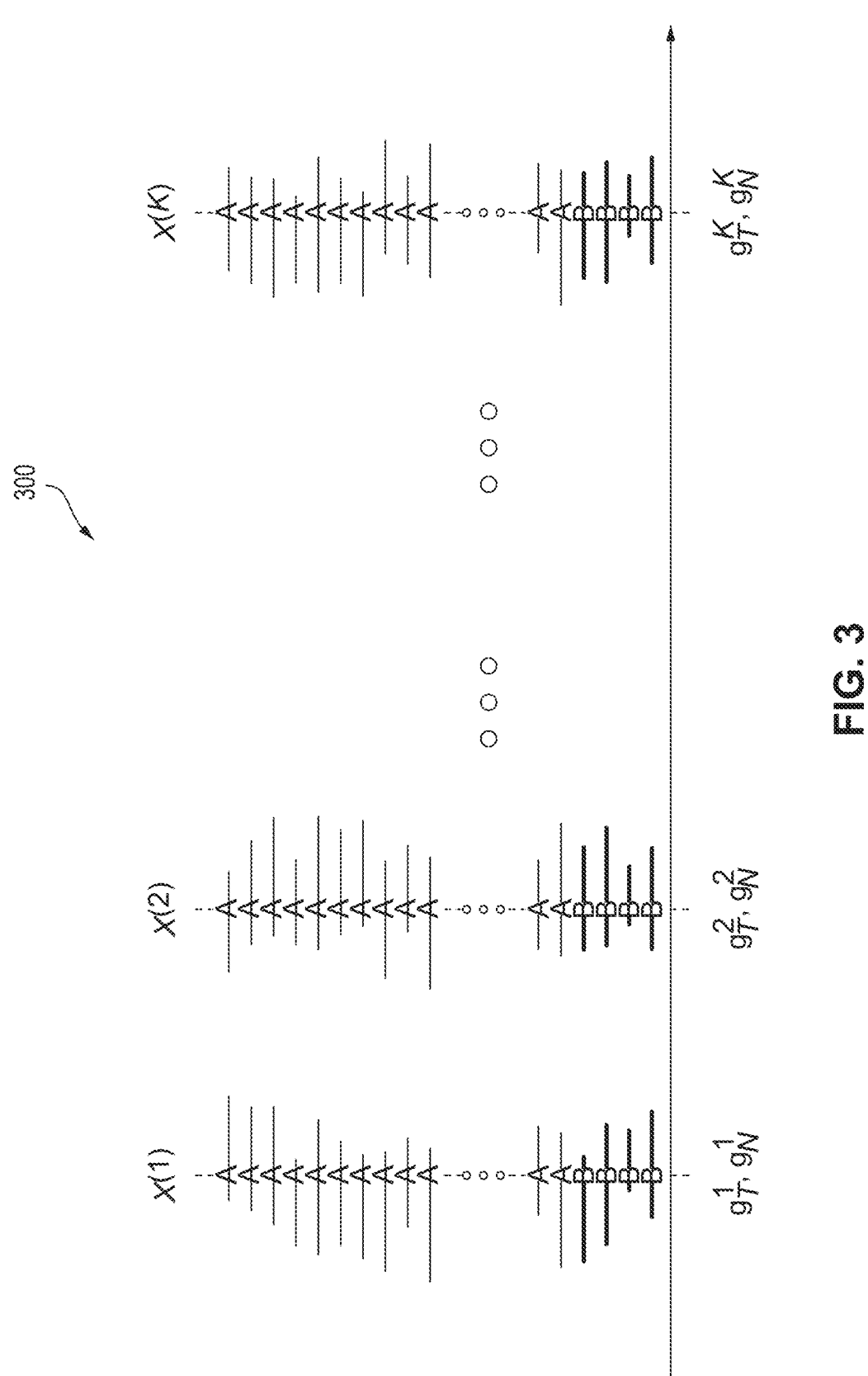
FIG. 3 illustrates certain concepts for estimating global tumor cfDNA fraction according to an embodiment.

Referring to diagram 300 of FIG. 3, $\theta$ can be approximated using the overall fraction of mutated reads for all possible hotspots, which may include loci which are highly likely to possess tumor variants. That is, FIG. 3 illustrates a concept where, for estimating global tumor cfDNA fraction, data sequencing includes sequencing reads at all hotspots, which are considered to have a lower effect of sequencing noise, e.g., sequencing errors.

A probabilistic method can be applied with consideration of possible sequencing errors. For example, $\theta$ can be estimated as the value that maximizes the likelihood $P(X|\theta)$, the 17 18 probability of observing sequencing data $X=(X^{(1)}, \ldots, X^{(K)})$ at K hotspots given the global tumor cfDNA fraction $\theta$.

The likelihood can be calculated by marginalizing the genotype G, $$P(X \mid \theta) = \prod_{r \in R_H} \sum_{G_{h(r)}} P(X_r \mid G_{h(r)}, \theta) P(G_{h(r)})$$

where $R_H$ represents a pool of reads covering at least one hotspot; $X_r$ represents information contained in read r; $G_{h(r)}$ represents the genotype of hotspots covered by read r; and h(r) is the set of hotspots that read r covers. Then the probability $P(X_r \mid G_{h(r)}, \theta)$ may be decomposed by further specifying the read origin (e.g., either tumor cells or normal cells). Further, where the global tumor cfDNA fraction is $\theta$, a random read from the sequencing data may have a probability of $\theta$ to be tumor-derived according to:

$$P(X_r \mid G_{h(r)}, \theta) = \theta P(X_r \mid g_{T_{h(r)}}) + (1-\theta) P(X_r \mid g_{N_{h(r)}}),$$

where $g_{T_{h(r)}}$ represents the joint tumor genotypes of hotspots on read r; while $g_{N_{h(r)}}$ represents the joint normal genotypes of hotspots h(r) on read r.

In some cases, different reads in $R_H$ can cover different hotspots (mutually exclusive) or have shared hotspots. Considering a maximum likelihood estimation framework, the joint combination of genotypes over all hotspots can be marginalized to eliminate the effect of genotypes. Because this step may include only the most suspicious loci, a single read may cover a tractable number of hotspots, thereby making such an approach reasonable for computation.

Single reads that cover more than one hotspot, can be considered as independent loci, instead of taking linkage disequilibrium into account which can further complicate the problem. Also, information in a read can be expanded to base calls, base qualities, and mapping qualities as well. This can be expressed by the following equation:

$$P\left(X_r \mid g_{T_{h(r)}}\right) = \prod_{k=1}^{K} P\left(X_r^{(k)} \mid g_T^{(k)}\right) = \prod_{k=1}^{K} P\left(B_r^{(k)}, Q_r^{(k)}, M_r \mid g_T^{(k)}\right)$$

where read r includes K hotpots, $$h(r) = \left(g_T^{(1)}r, \ldots, g_T^{(K)}\right); X_r^{(k)}$$

represents the information of the base covering hotspot k on read r; $B_r^{(k)}$, $Q_r^{(k)}$, and $M_r$ represent the base call, the base quality at hotspot k, and the mapping quality of read r, respectively, and $$g_T^{(k)}$$

represents tumor genotype at hotspot k. This may hold true for a normal scenario. This can be expressed by the following equation:

$$P(X_r \mid g_{N_r}) = \prod_{k=1}^{K} P\left(B_r^{(k)}, Q_r^{(k)}, M_r \mid g_{N_r}^{(k)}\right)$$

where $$g_{N_r}^{(k)}$$

represents a normal genotype at hotspot k.

From the foregoing, the probability of observing a base in sequencing data given the genotype may be computed. An assumption may be made that, for a given hotspot, a read with base A is observed, while the genotype given is AB. Then the base can be determined from allele A with probability $\frac{1}{2}$ P (sequencing correctly), and comes from allele B with probability $\frac{1}{2}(\frac{1}{3}$ P(sequencing wrongly)), where the value $\frac{1}{3}$ represents all three (3) possible incorrect base calls. However, instead of simply using $\frac{1}{3}$, uneven probabilities can be used to account for the different tendencies of sequencing errors. This can be expressed by the following equation:

$$P(A, Q_r^{(k)}, M_r \mid AB) = \frac{1}{2}P(A, Q_r^{(k)}, M_r \mid A) + \frac{1}{2}P(A, Q_r^{(k)}, M_r \mid B) = \frac{1}{2}(1-\epsilon) + \frac{1}{2}(\frac{1}{3}\epsilon)$$

where $\epsilon$ represents the probability that the base comes from a sequencing error. Also, $P(A, Q^{(k)}, M_r \mid A)$ represents the probability of observing an A base with quality $Q_r(k)$, $M_r$ if the base comes from sequencing allele A, while $P(A, Q^{(k)}, M_r \mid B)$ represents the probability of observing an A base with quality $Q_r^{(k)}$, $M_r$ if the base comes from sequencing allele B. As such, the foregoing equation can account for both possible origins of base A. The base quality and the mapping quality can be indicative of the probability of a wrongly-sequenced base or a wrongly-placed read in the Phred scale, so they can be transferred transferred back to probabilities. This can be expressed by the following equation:

$$\epsilon(Q_r^{(k)}, M_r) = 1 - \left(1 - 10^{-\frac{M_r}{10}}\right)\left(1 - 10^{-\frac{Q_r^k}{10}}\right)$$

By solving the above equations, the estimation of a global tumor cfDNA fraction can be performed with a high degree of accuracy (e.g., an accuracy of at least 80%, 90%, 95%, 96%, 97%, 98%, 99%, or more).

The probability of observing such a sequencing dataset can be calculated by quantifying the probability of sequencing errors and mapping errors, assuming that reads and hotspots are independent of one another. Alternatively, a simplified approach can be used, where global tumor cfDNA fraction is estimated as the maximum of variant allele frequencies among the loci. Even if the precision of tumor cfDNA fraction estimation is not optimized, the accuracy of SNV calling may not be meaningfully decreased as long as the estimated tumor cfDNA fraction is correct in scale.

Genotype calculation block 203 can use information received from tumor cfDNA fraction estimation block 202 to calculate a probability of normal, tumor, and joint genotypes. The framework for calculating genotypes (or calling SNVs) may comprise calculating a genotype likelihood at locus k, $$k, P(X^{(k)} \mid G^{(k)}) \text{ as } P(X^{(k)} \mid G^{(k)}) = \prod_{r=1}^{n} P(X_r^{(k)} \mid G^{(k)}),$$

where $X^{(k)}$ represents the observed set of n sequencing reads $$X^{(k)} = \left(X_1^{(k)}, \dots, X_n^{(k)}\right)$$

covering a specific site on the genome.

Figure 4:
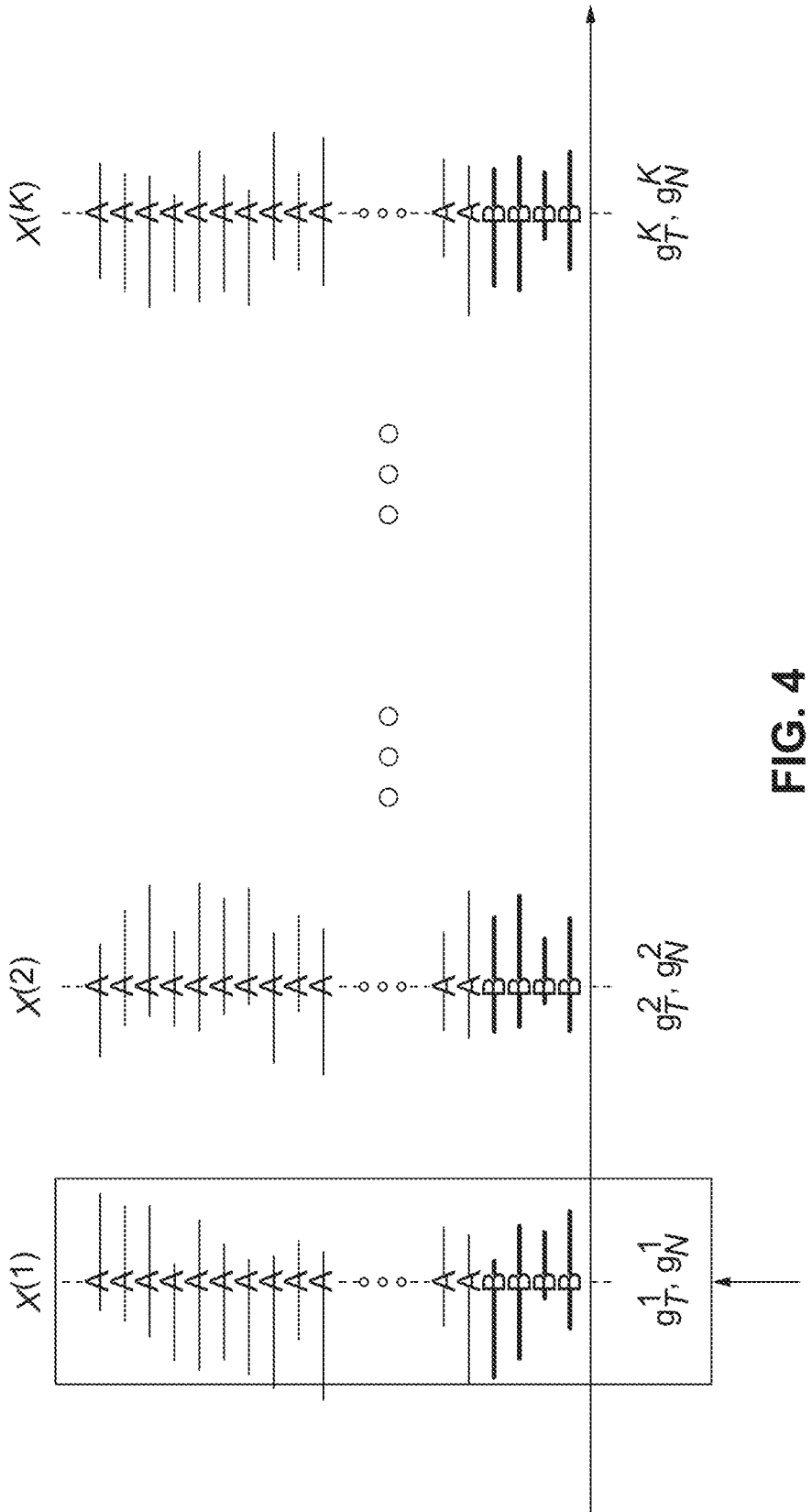
FIG. 4 illustrates certain concepts of investigating a locus according to an embodiment.

This concept is illustrated, in part, by FIG. 4, which shows a chart. Referring to FIG. 4, only the base covering the investigated locus on a read may be considered when identifying somatic SNVs. As shown, for each sequencing read, $X^{(k)}$, a tumor genotype $g_{T_r}^{(k)}$ is investigated, where sequencing allele A is shown by solid lines and sequencing allele B is shown by dashed lines.

According to an embodiment, maximizing a posterior is performed in order to predict the joint normal-tumor genotype. The joint normal-tumor genotype having the highest posterior probability, given the observed sequencing data, may be considered the true genotype of the sample.

When analyzing cfDNA, the genotype likelihood may need to incorporate the low frequency of tumor DNA by adding the new parameter θ. This can be expressed by the following equation:

$$P(X^{(k)} \mid G^{(k)}, \theta) = \prod_{r=1}^{n} P(X_r^{(k)} \mid G^{(k)}, \theta)$$

Generally, the likelihood of each read r that covers locus k can be decomposed into respective likelihoods: $g_N^{(k)}$ $^{and}$ $g_T^{(k)}$. This can be expressed by the following equation:

$$P(X_r^{(k)} \mid G, \theta) = P(\text{read } r \text{ is from normal } cfDNA)P\left(X_r^{(k)} \mid g_N^{(k)}\right) +$$
$$P(\text{read } r \text{ is from tumor } fDNA)P\left(X_r^{(k)} \mid g_T^{(k)}\right)$$

Note that the prior probability P(read r is from tumor-derived cfDNA) may actually be the prior allele frequency θ of $g_T^{(k)}$ at the current site k. This approach may yield:

$$P\left(X^{(k)} \mid G, \theta\right) = (1 - \theta)P\left(X_r^{(k)} \mid g_N^{(k)}\right) + \theta P\left(X_r^{(k)} \mid g_N^{(k)}\right).$$

In the foregoing equation, $$P\left(X_r^{(k)} \mid g_N^{(k)}\right) \text{ or } P\left(X_r^{(k)} \mid g_T^{(k)}\right)$$

may be the same as that calculated in the foregoing discussion.

However, in contrast to estimating global tumor cfDNA fraction, when genotyping (e.g., calling SNVs), only the base at the genotyped locus may matter on a single read. Then, using a Bayesian theorem, the posterior genotype $G^{(k)}$ at locus k that maximizes posterior probability can be estimated. This can be expressed by the following equation:

$$P(G^{(k)} \mid X^{(k)}, \theta) \propto P(X^{(k)} \mid G^{(k)}, \theta)P(G^{(k)})$$

$$P\left(g_T^{(k)}, g_N^{(k)} \mid X^{(k)}, \theta\right) \propto$$
$$P\left(g_T^{(k)}, g_N^{(k)}\right) \prod_{read\ r} \left\{(1 - \theta)P\left(X_r^{(k)} \mid g_N^{(k)}\right) + \theta P\left(X_r^{(k)} \mid g_T^{(k)}\right)\right\}$$

The prior distribution of joint normal-tumor genotype G may be determined before calculation. For example, if the interesting loci are annotated in public cancer mutation databases, e.g. Single Nucleotide Polymorphism Database (dbSNP, www.ncbi.nlm.nih.gov/projects/SNP/), or Catalogue of Somatic Mutations in Cancer (COSMIC, cancer.sanger.ac.uk/cosmic), then the variant allele frequency in general population can be directly acquired. Alternatively, sequencing data in public data sources, such as The Cancer Genome Atlas database (TCGA, cancergenome.nih.gov/), 1000 Genome database (www.internationalgenome.org/), and The International Cancer Genome Consortium database (ICGC, icgc.org/), can be explored. By considering the specific locus over a group of samples, the allele frequency of a segment of the population or a group of subjects (e.g., patients) can be determined.

To detect tumor-derived SNV from cfDNA, germline polymorphism may be eliminated. This may be performed by considering both the normal genotype and the tumor genotype, thereby considering germline polymorphisms.

Referring again to FIGS. 2A-2E, at block 201, the information from the normal blood cells (such as white blood cells) of the same subject can be used to incorporate normal reads into the analysis framework. That is, this information can be used to further calculate the likelihood of normal, tumor, or joint genotypes. This may be a similar scenario as the germline SNV removal in matched tumor-normal tissue sample. The posterior probability can be changed to:

$$P\left(X_w^{(k)}, X_P^{(k)} \mid G^{(k)}, \theta\right) = P\left(X_P^{(k)} \mid G^{(k)}, \theta\right)P\left(X_w^{(k)} \mid g_N^{(k)}\right)$$

where $X_w^{(k)}$ is the data from matched normal sample such as white blood cells, and $X_P^{(k)}$ represents cfDNA reads sequenced from plasma.

Filtration block 204 may perform post-call filtration. A set of filters may be developed to remove unreliable mutation candidates for cfDNA data. Base qualities and mapping qualities may be important for removal of low quality reads, containing sequencing errors. The probabilistic model can incorporate such quality scores. Apart from a type of errors that can be distinguished by quality scores, there may also exist systematic errors that cannot be eliminated by using only quality scores. Embodiments may combine the read information nearby a mutation candidate, and may filter low quality mutation candidates by all reads observed at the locus.

Strand bias filters may be applied by filtering mutation candidates if they meet one of the following criteria: (1) a percentage of reads from a single strand being larger than a threshold; (2) reads containing the variant allele being observed from a single strand; (3) a proportion of reads containing variant alleles among all non-reference reads being above a given threshold; and (4) a ratio of reads containing non-reference alleles on strands being above a given threshold.

Base quality filters may be applied by comparing base quality between candidates and their adjacent loci. Mutation candidates may be filtered if they meet one of the following criteria: (1) T-statistic of base qualities at the locus and its adjacent locus being above a given threshold; and (2) a T-statistic of non-reference base qualities at the locus and its adjacent locus being above a given threshold.

Read mate filters may be applied by excluding the read mates in the following filtration, if the read mates are inconsistent at their overlapping sequences.

Sequence context can also affect sequencing error rates. As such, sequence context filters may be applied by identifying mutation candidates that are close to an area or within a homopolymer.

Sequencing error filters may be applied based on a machine learning model. Referring to FIGS. 2A-2E, at block 206, a machine learning model is trained to classify reads having true variants and reads having sequencing errors. Reads classified as containing sequencing errors may be eliminated in the following filtration. A classifier may be trained to classify reads containing tumor-derived mutations and sequencing errors based on their intrinsic difference in multiple aspects, such as base qualities, sequencing contexts, PHRED scores, etc. In particular, different features may be extracted of an allele in the read, such as: read alignment related features (such as alignment quality and alignment information of each surrounding base that is encoded in CIGAR string in the SAM file), genomic context surrounding this allele (such as read sequence and insertions/deletions), sequencing quality of each base in the read, and insert size for paired-end sequencing data.

Figure 5:
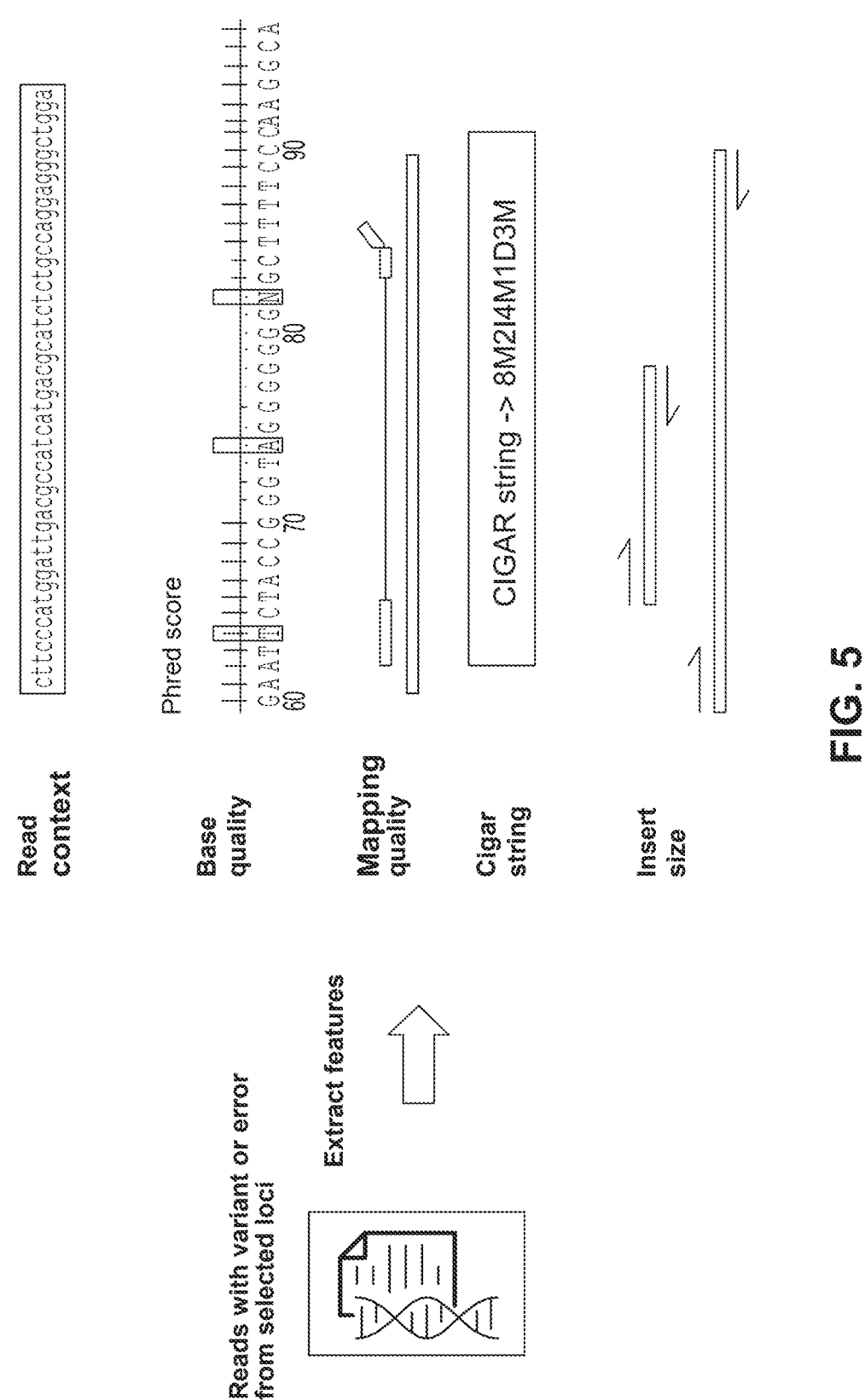
FIG. 5 illustrates the procedure of extracting features for the machine learning model that can distinguish true variants and sequencing errors based on the individual read information according to an embodiment.

FIG. 5 illustrates a procedure of extracting features for the machine learning model. Referring to FIG. 5, this feature profile is input to the classifier for discriminating signal and error. Since the cfDNA may be fragmented naturally with a length distribution centered around about 166 base pairs (bp), paired end read mates can have overlapping bases after mapping to the reference. The overlapping bases can be sequenced both from the forward strand and the reverse strand of the same cfDNA fragment, so such bases can provide extra information or confirmation that they are at variant loci. Hence, features extracted from read mates may be combined together. For evaluating the effectiveness of this feature profile, a conventional classification method. (e.g., random forest) may be used to evaluate how distinguishable the extracted features. are. Results may illustrate that such a feature profile achieves good performance.

In addition to traditional classifiers, different classifiers, such are more complex classifiers (e.g., a deep learning classifier) may be used to further boost the discrimination performance of true mutations and sequencing errors. The deep learning model can comprise any descent architecture of deep artificial neural networks, such as the Convolutional Neural Network (CNN) based classifier. A CNN-based classifier may be used, which comprises (1) convolution layers, (2) sub-sampling layers that can extract informative and abstract features at different scales, and (3) output prediction layers that can use extracted features for final predictions of true mutations and sequencing errors. These layers may be stacked to form the deep neural network, and their parameters can be learned by stochastic gradient-based optimization algorithms. For example, such CNN-based architecture can be applied toward imaging classification applications.

For training the machine learning model, high-quality ground-truth training data may be required, which includes the reads that have been validated to have either sequencing errors or true variants. Such ground truth data may be obtained by using different sequencing data from the same sample with enough coverage, e.g. whole exome sequencing data and high coverage PCR-free whole genome sequencing data, obtained from NA12878 in the 1000 Genomes project and a metastatic breast cancer patient (MBC315). Variants in the target region of whole exome sequencing may be called from both samples individually. Those reads containing variants identified with high confidence in both samples may be regarded as training data of the reads with true variants, while those reads containing variants identified in one sample with low confidence may be regarded as training data of the reads with sequencing errors.

Figure 6:
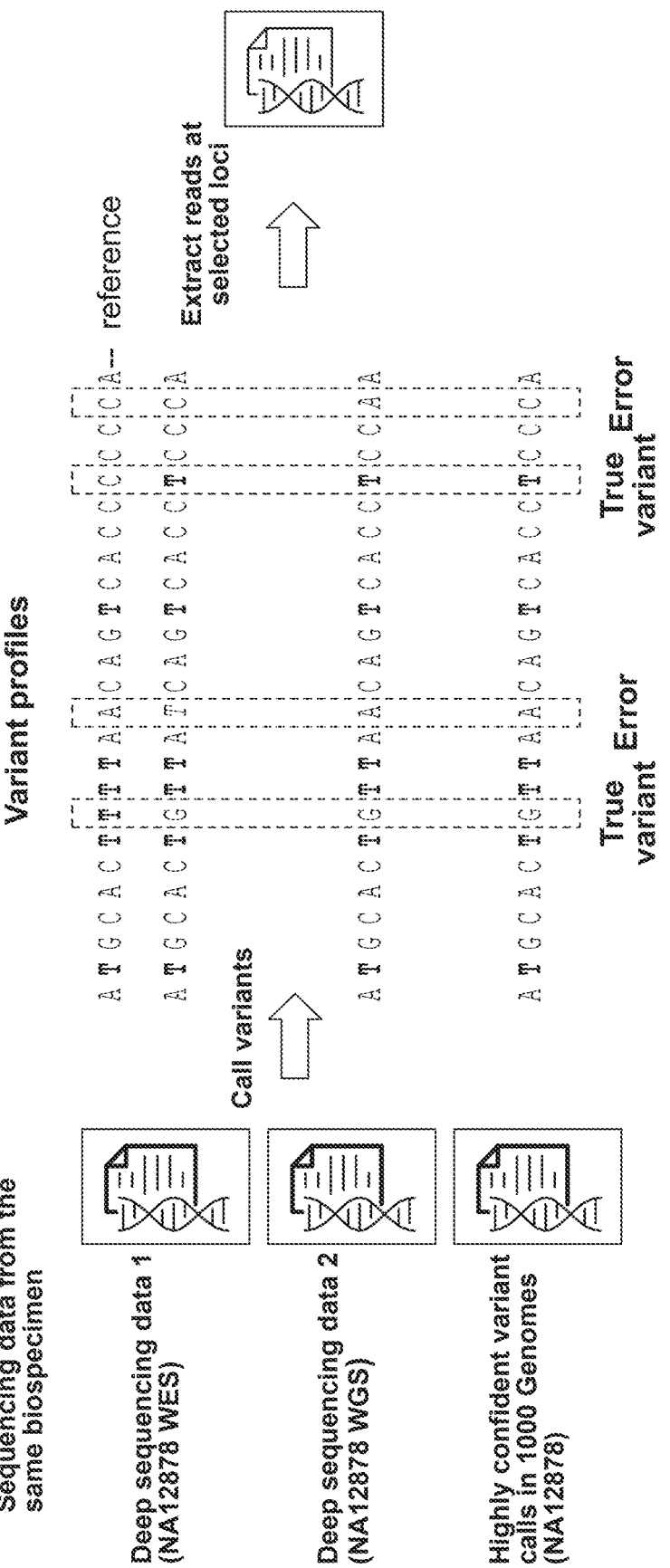
FIG. 6 illustrates the procedure of training data generation for the machine learning model that can distinguish true variants and sequencing errors based on the individual read information according to an embodiment.

Aspects of collecting the training data using NA12878 are illustrated by FIG. 6. That is, FIG. 6 illustrates a procedure for training data generation for the machine learning model.

Known SNP filters may be applied by filtering mutation candidates that are observed in public databases, such as dbSNP, The Exome Aggregation Consortium Database (ExAC, exac.broadinstitute.org/), and The Genome Aggregation Database (gnomAD, gnomad.broadinstitute.org/). Candidates that are observed in COSMIC may be retained.

After somatic SNVs are called between a solid tumor tissue (resected in surgery or biopsy) and a normal blood sample, the estimation of the global tumor fraction (block 205 of FIGS. 2A-2E) can be further refined using the somatic SNVs identified from the above steps: blocks 202, 203, and 204. In particular, truncal mutations can be selected for monitoring, from the called somatic mutations with their variant allele frequencies calculated. Solid tumor tissue may not be required in this step. A number of truncal mutations may be combined to ensure sensitive detection of a small fraction of tumor-derived cfDNA.

Application for Detecting MRD: A cfDNA-Based Monitoring Approach

As shown at block 207, this approach may have a wide range of applications, such as cancer detection, monitoring, prognosis, and more specifically blood tumor mutation burden (bTMB) calculation, MRD detection and resistance monitoring. For example, MRD detection is an application that can demonstrate the clinical usage of methods and systems of the present disclosure.

Figure 7:
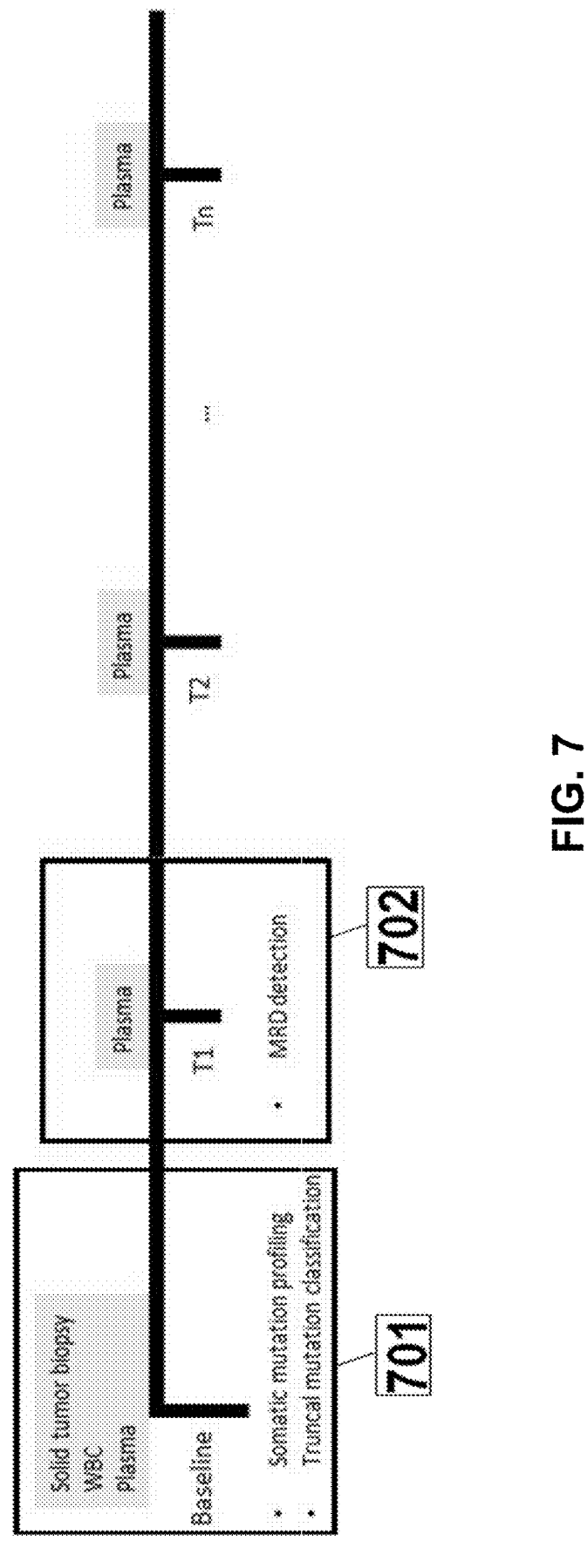
FIG. 7 illustrates a timeline of performing early detection of minimal residual disease (MRD) according to an embodiment.

FIG. 7 illustrates a timeline of performing early detection of minimal residual disease (MRD). As shown in FIG. 7, the timeline of using methods and systems of the present disclosure for MRD detection may include two steps. At block 701, truncal mutations and the mutation profile from pre-surgery plasma cfDNA samples ("baseline" samples) may be identified. Since plasma cfDNA contains DNA fragments derived from multiple tumor sites, a comprehensive tumor mutational profile (SNVs and their variant allele frequencies) that are calculated in the subject's pre-surgery plasma cfDNA sample can be used to identify "truncal mutations," which generally refers to those variants with high variant allele frequencies among all detected variants.

In particular, cfDNA SNV detection methods may be applied to a pre-surgery plasma cfDNA sample and its matched normal sample (e.g., white blood cells from the same subject) to identify all somatic SNVs and their variant frequencies. Then truncal mutations may be selected based on the mutation calling results from the cfDNA and the matched normal sample (e.g. from white blood cells), and their variant allele frequencies can be calculated.

Alternatively, somatic SNVs called from solid tumor tissue (resected in surgery or biopsy) and its matched normal sample can be used to determine a set of truncal mutations. Many different mutation calling tools can be used (e.g. VarScan2, MuTect, SomaticSniper, etc.) to call somatic SNVs. However, truncal mutations cannot always be determined from solid tumor tissues taken from a single tumor site. Hence, solid tumor tissue may not be required for methods and systems of the present disclosure to be effective. Further, truncal mutations may be determined based only on mutation calling results from blood samples (e.g., plasma cfDNA and white blood cell DNAs).

At block 702, minimum residual disease (MRD) is detected using follow-up plasma cfDNA samples. That is, after surgery, the follow-up plasma samples can be used to monitor and detect MRD. Because the tumor has been treated or resected, the tumor fraction in the follow-up plasma may be lower than in the baseline plasma. Variant allele frequency may be at the same scale as, or even lower than the sequencing error rate. Therefore MRD detection may require the sensitive and reliable detection of reads containing true mutations, using, for example, the machine learning method for distinguishing true mutations from sequencing errors. (as described by block 206 of FIGS. 2A-2E). In particular, this machine learning method can be applied to extract those reads that cover the position of identified truncal mutations and are classified as carrying true variants. Then, only those reads classified as containing true variants may be used for calculating the MRD predictive score (or called MRD index score). This score may be defined as the proportion of reads containing truncal mutations among the reads covering truncal mutations.

Figure 8A:
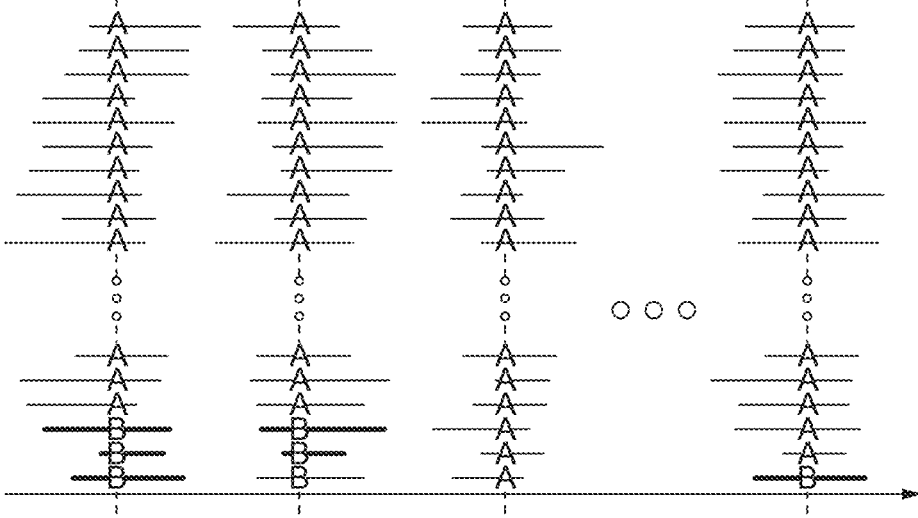
FIGS. 8A-8B illustrate certain components of a system for performing early detection of minimal residual disease according to an embodiment.
Figure 8B:
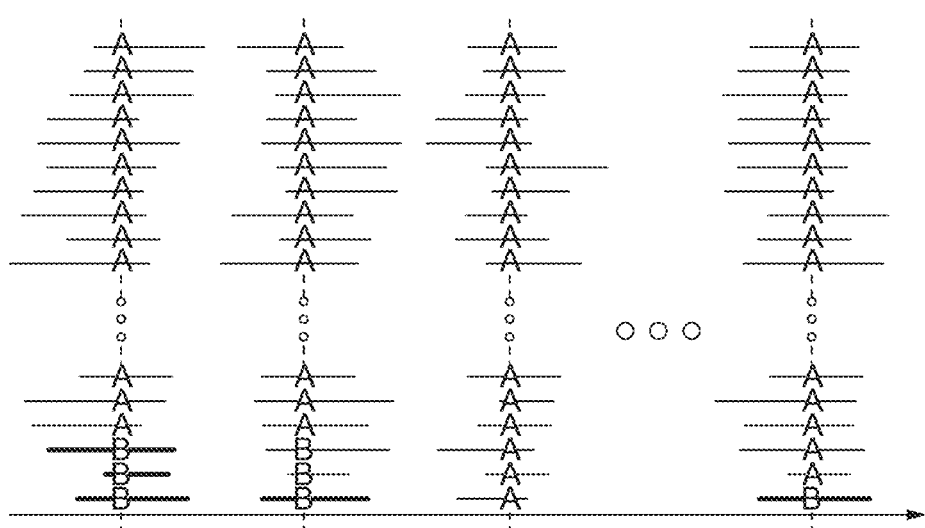
Figure 8B:
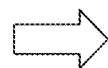
Figure 8B:
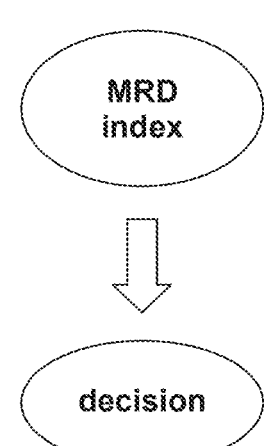

FIGS. 8A-8B illustrate the foregoing in greater detail. That is, FIGS. 8A-8B illustrate certain components of a system for performing early detection of minimal residual disease (MRD).

To assess the statistical significance of the MRD predictive score in determining the tumor presence, a within-sample background distribution generation method may be used to model the normal background without introducing extra experimental bias and requiring extra cohort of samples. An assumption may be made that k truncal mutations are identified, and k sites may be randomly sampled in the genome that do not include the identified mutations but match the characteristics of those k truncal mutations (e.g. the number of mutations, the distribution of nucleotides, and the depth of coverage). Reads covering the randomly sampled k sites may be extracted and then fed into the sequencing error suppression workflow to filter out sequencing errors. An MRD predictive score may be generated for the k sampled sites. The sampling may be repeated N times (e.g., where N is at least about 5, about 10, about 25, about 50, about 100, or more than about 100), and generate N MRD scores. These N MRD predictive scores may comprise a background distribution to evaluate the statistical significance of the MRD predictive score of the k truncal mutations. This step may be repeated over time to detect the minimal residual disease (MRD).

Nucleic Acid Sequencing

Samples of the present disclosure may be sequenced using various nucleic acid sequencing approaches. Such samples may be processed prior to sequencing, such as by being subjected to purification, isolation, enrichment, nucleic acid amplification (e.g., polymerase chain reaction (PCR)). Sequencing may be performed using, for example, Sanger sequencing, high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing (e.g., Illumina, Pacific Biosciences of California, Ion Torrent), Single Molecule Sequencing by Synthesis (SMSS)(Helicos), massively-parallel sequencing, Clonal Single Molecule Array (Solexa), shotgun sequencing, Maxim-Gilbert sequencing, primer walking, sequencing using PacBio, SOLiD, Ion Torrent, or Nanopore platforms and any other sequencing methods known in the art. Simultaneous sequencing reactions may be performed using multiplex sequencing.

Sequencing may generate sequencing reads ("reads"), which may be processed by a computer. In some examples, reads may be processed against one or more references to identify single nucleotide variants (SNVs).

In some examples, sequencing can be performed on cell-free polynucleotides that may comprise a variety of different types of nucleic acids. Nucleic acids may be polynucleotides or oligonucleotides. Nucleic acids included, but are not limited to deoxyribonucleic acid (DNA) or ribonucleic acid (RNA), single-stranded or double-stranded DNA, complementary DNA (cDNA), or a RNA/cDNA pair.

Results

The performance of methods and systems of the present disclosure in detecting somatic SNVs are compared to results of four selected methods (SiNVICT, VarScan 2, MuTect, and MuTect 2) under identical test conditions.

Simulation Results on Data Generated From Wgsim

The sequencing reads in the first simulation dataset are generated from wgsim. The reads containing reference sequences and the reads containing variant alleles are mixed with predefined ratios, 0.1%, 0.5%, 1%, and 5%. The low variant allele frequency may mimic the conditions encountered in cfDNA sequencing data.

In the first simulation, results obtained using methods and system of the present disclosure are compared against VarScan2 and SiNVICT on the simulated data, which was obtained by applying wgsim on a human reference genome (hg19). In particular, a region (chr19:10602252-10602938) with known pathogenic mutations of non-small cell lung cancer (NSCLC) and simulated ultra-deep sequencing is extracted. Thirteen somatic variants are added to this region.

The average read depth obtained is ~1448 in four different tumor-derived cfDNA fractions (5%, 1%, 0.5%, 0.1%). To better approximate the real reads, sequencing errors and indels are introduced into the reads. As illustrated by Table 1, for samples with low tumor cfDNA fraction, methods and systems of the present disclosure perform better than the other two methods. That is, the simulation results show that methods and systems of the present disclosure are able to meaningfully detect SNVs from plasma DNA with very low ctDNA fractions, in contrast to other approaches.

TABLE 1

| tumor cfDNA fraction | 0.10% | 0.50% | 1% | 5% |
|---|---|---|---|---|
| Described Embodiments | 0% | 46% | 62% | 100% |
| VarScan2 (p <0.05) | 0% | 15% | 62% | 85% |
| SiNVICT | 0% | 0% | 46% | 85% |

Table 1 illustrates the precision of three methods on simulated sequencing samples with different tumor cfDNA fractions. Note that recalls are not shown in Table 1, since all methods demonstrated perfect recall for simulated reads.

Simulation Results on Data Generated from a Metastatic Cancer Patient

The second simulation dataset comprises a spike-in dataset from whole exome sequencing data of buffy coat samples and metastatic tumor samples from the same subject. The sample mixing ratios are set to ensure variant allele frequencies of the somatic SNVs in the subject's genome at about 20%, 10%, 5%, and 1%.

In the second simulation, methods and systems of the present disclosure are tested on real whole exome sequencing data from a metastatic cancer patient. The real sample may comprise greater complexity than the simulated reads. Exon regions in 7 genes reported to have somatic mutations in cfDNA are extracted, where six of the seven are identified in liver metastasis sampled, and the remaining one is only detected in primary breast cancer.

To obtain samples with different tumor-derived cfDNA fractions, the buffy coat samples are mixed with liver metastasis samples with different spike-in ratios. The first spike-in samples are in six different tumor-derived cfDNA fractions (approximately 20%, 10%, 5%, and 1%), assuming all somatic variants are heterozygous. The read depth at the mutation loci ranges from 46 to 195. Therefore, the somatic variant, which only occurs in the primary breast cancer sample, is regarded as a control that should not be identified in spike-in samples.

As shown in Table 2, in the sample with 10% tumor cfDNA fraction, methods and systems of the present disclosure did not detect a somatic variant with variant allele frequency 1%. In real sequencing samples, although the overall tumor cfDNA fraction may be as high as 10%, the variant allele frequency may be low for a given locus. When the tumor cfDNA fraction is lower, the spike-in samples do not contain any reads supporting variant allele at most of the somatic variant loci.

SiNVICT performs moderately on simulated sequencing data, but poorly on real sequencing data. It recognizes all somatic variants as germline variants.

TABLE 2

|  | tumor cfDNA fraction | Methods of the Present Disclosure | VarScan2 | SiNVICT | MuTect | MuTect2 |
|---|---|---|---|---|---|---|
| precision | 20% | 100% | 83% | 0% | 100% | 100% |
| recall | 20% | 100% | 100% | 0% | 100% | 100% |
| precision | 10% | 83% | 67% | 0% | 17% | 67% |
| recall | 10% | 100% | 100% | 0% | 100% | 100% |
| precision | 5% | 67% | 33% | 0% | 0% | 33% |
| recall | 5% | 100% | 0% | 0% | 0% | 100% |
| precision | 1% | 17% | 0% | 0% | 0% | 0% |
| recall | 1% | 9% | 0% | 0% | 0% | 0% |

Table 2 shows the precision and recall of three methods on real sequencing data with different tumor cfDNA fraction. The read depth ranges from 46 to 195.

The computational approach of SiNVICT, which is designed for detection of somatic SNV from cfDNA, fails most of the time for the early cancer detection, e.g., when the tumor cfDNA fraction is relatively low. The other approach, CAPP, which combines both experimental design and computational methods, fails at least half of the time in early cancer detection as well, even with 10 k coverage at genotyped loci.

In contrast, methods and systems of the present disclosure achieved comparable somatic SNV detection with 7 to 70 times fewer coverage. Moreover, special sequencing design or targeted panel may not be required to perform the analyses. Therefore, methods and systems of the present disclosure can be applied to general cancer detection or screening, instead of specific detection of a single cancer type. This is because the whole exome sequencing data can be accepted as input. If a particular cancer type is specified for examination using methods and systems of the present disclosure, a genotyping panel can be designed for somatic SNV detection.

A sample is obtained from a 41-year-old female diagnosed with ER+HER2+ breast cancer, which has spread to the lymph nodes. Blood is collected approximately 30 minutes before a liver biopsy is taken to yield a metastasis sample. From sequencing results, an average variant allele percentage of 14% is obtained in cfDNA, indicating that approximately 28% of cfDNA is of tumor origin. The blood sample is obtained at a late stage of cancer, so the percentage of tumor DNA is not relatively low.

The sequencing statistics of the samples analyzed are shown in Table 3 and Table 4.

TABLE 3

| Tissue | Input DNA(ng) | Reads(Millions) | Mapped reads(%) | Paired reads(%) |
|---|---|---|---|---|
| Buffy Coat | 412 | 182 | 181(99.6) | 180(98.8) |
| Primary Tumor | 301 | 112 | 110.8(99.2) | 99.1(88.8) |
| Metastasis | 341 | 173 | 171.8(99.5) | 170(98.6) |
| cfDNA | 155 | 286 | 284.8(99.5) | 253(88.5) |

TABLE 4

| Tissue | On target mapped reads(%) | PCR duplicates | Mean sequencing depth |
|---|---|---|---|
| Buffy Coat | 154(84.8) | 0.2 | 201 |
| Primary Tumor | 92(82.8) | 0.52 | 118 |
| Metastasis | 140(81.6) | 0.22 | 183 |
| cfDNA | 239(83.8) | 37% | 309 |

As described in the present disclosure, cfDNA provides unique opportunities for cancer diagnosis, prognosis, and precision oncology. However, current computational tools for analyzing mutations, specifically for ctDNA in plasma, may not be optimally accurate. Methods and systems of the present disclosure may use a Bayesian-based probability framework to estimate the likelihood of a genotype, given a set of sequencing data. A maximizing a posterior estimation may be used for identifying the genotype of subjects (e.g., patients) and calling somatic SNVs. Both sequencing errors and low tumor variant allele frequencies in plasma samples may be taken into consideration, thereby aiding the detection of somatic SNV, and ensuring good performance.

As seen from simulation results (e.g., using either spike-in real sequencing data or simulated sequencing data), methods and systems of the present disclosure may outperform other approaches because they can account for cfDNA's special biological properties. Since methods and systems of the present disclosure can detect somatic SNVs from low tumor cfDNA fraction plasma samples, they can be applied to early cancer diagnosis with liquid biopsy and cancer post-treatment monitoring. With certain driver mutations detected, clinicians can determine cancer types, and provide personalized treatment to patients.

Simulation Results Generated on Data by Mixing Two Germline Samples

To simulate different dilutions of ctDNA in plasma, two high quality germline samples obtained from public databases (e.g., normal (NA24385) and tumor (NA12878)) are mixed. Somatic mutations may include 679 high quality mutations identified by VarScan in NA12878 (as tumor), but not in NA24385 (as normal).

According to simulations, 20 samples may be generated for dilution (e.g., 0.001%, 0.002%, 0.005%, 0.008%, 0.01%, 0.02%, 0.05%, 0.08%, 0.1%, 0.2%, 0.5%, 0.8%, and 1%). For example, a sample may be identified as being indicative of resistance if the p-value of the test is no more than about 0.05.

Figure 9:
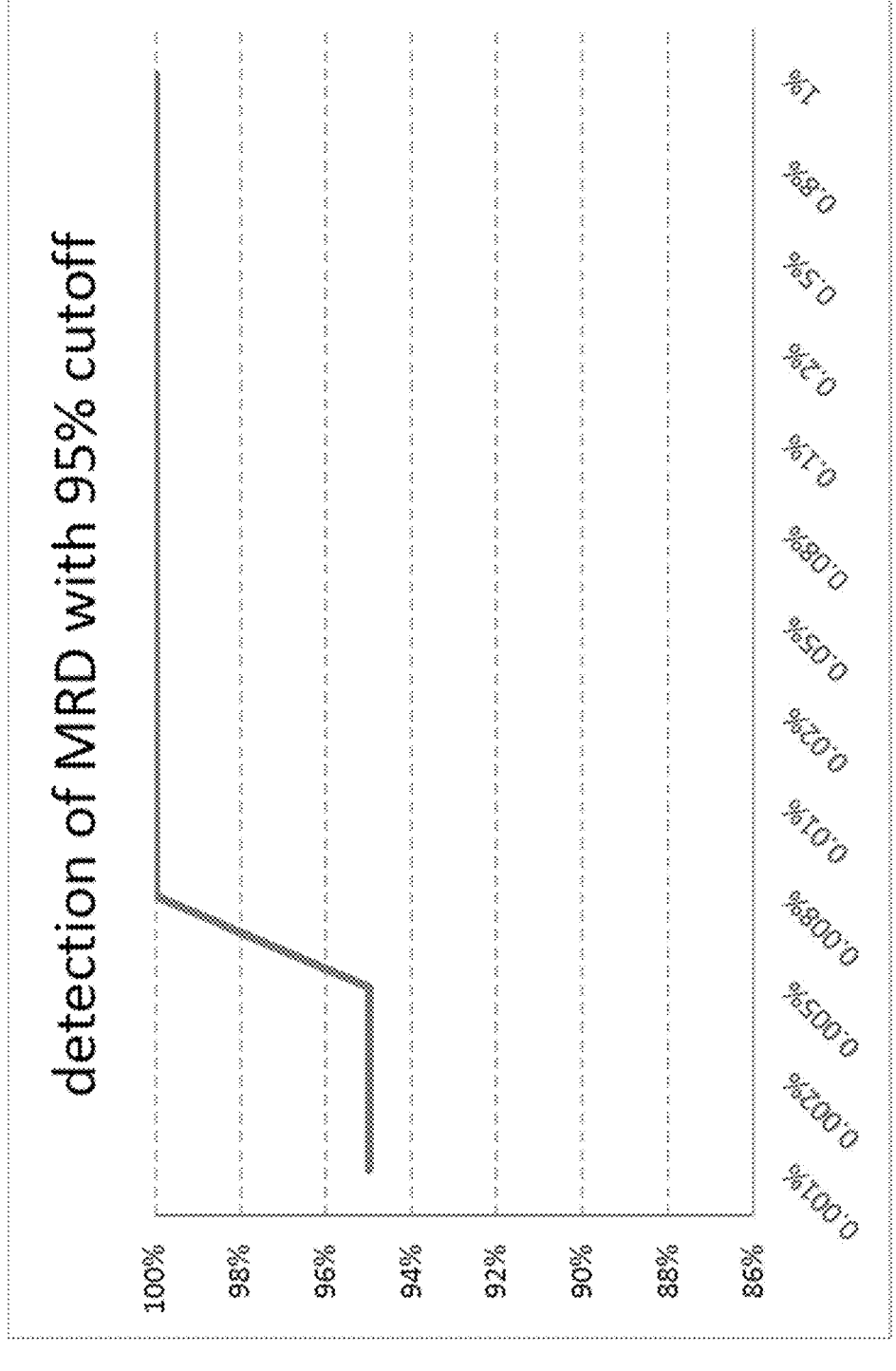
FIG. 9 illustrates aspects of detection of minimal residual disease using disclosed methods according to an embodiment.

FIG. 9 illustrates a performance 900 of detection of minimal residual disease (MRD) using methods and systems of the present disclosure. As shown by. FIG. 9, MRD can be perfectly detected in samples having a tumor fraction (TF) as low as about 0.008%. Thus, methods and systems of the present disclosure may be applied to toward early detection of MRD.

Figure 10:
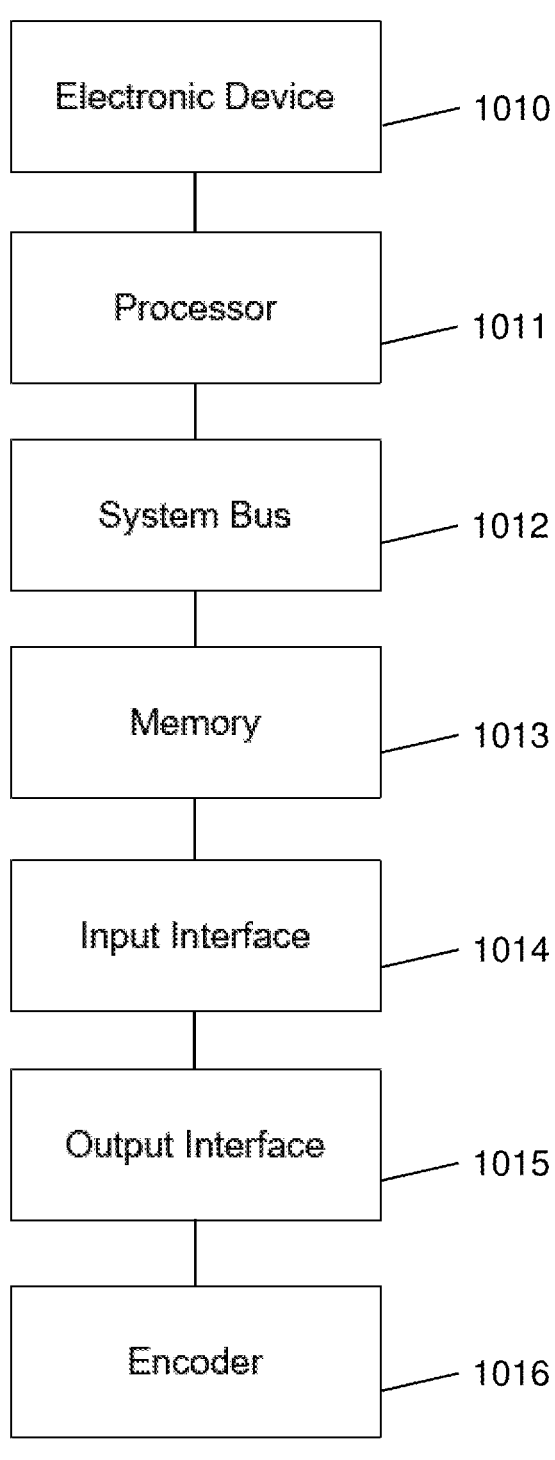
FIG. 10 illustrates certain components of a system for performing disclosed methods according to an embodiment.

FIG. 10 shows an example system adapted to detect somatic single nucleotide variants (SNVs) from cell-free nucleic acid, such as deoxyribonucleic acid (cfDNA) and ribonucleic acid (cfRNA), according to methods of the present disclosure. Electronic device 1010 can comprise various configurations of devices. For example, electronic device 1010 can comprise a computer, a laptop computer, a tablet device, a server, a dedicated spatial processing component or device, a smartphone, a personal digital assistant (PDA), an Internet of Things (IoT or IOTA) device, a network equipment (e.g., router, access point, femtocell, Pico cell, etc.), and/or the like.

Electronic device 1010 can comprise any number of components operable to facilitate functionality of electronic device 1010 according to methods of the present disclosure, such as processor(s) 1011, system bus 1012, memory 1013, input interface 1014, output interface 1015, and encoder 1016 of the illustrated embodiment. Processor(s) 1011 can comprise one or more processing units, such as a central processing unit (CPU) (e.g., a processor from the Intel CORE family of multi-processor units), a field programmable gate array (FPGA), and/or an application specific integrated circuit (ASIC), operable under control of one or more instruction sets defining logic modules configured to provide operation as described herein. System bus 1012 couples various system components, such as memory 1013, input interface 1014, output interface 1015 and/or encoder 1016 to processor(s) 1011. Accordingly, system bus 1012 of embodiments may be any of various types of bus structures, such as a memory bus or memory controller, a peripheral bus, and/or a local bus using any of a variety of bus architectures. Additionally or alternatively, other interface and bus structures, such as a parallel port, game port or a universal serial bus (USB) may be utilized. Memory 1013 can comprise various configurations of volatile and/or non-volatile computer-readable storage media, such as RAM, ROM, EPSOM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Input interface 1014 facilitates coupling one or more input components or devices to processor(s) 1011.

For example, a user may enter commands and information into electronic device 1010 through one or more input devices (e.g., a keypad, microphone, digital pointing device, touch screen, etc.) coupled to input interface 1014. Image capture devices, such as a camera, scanner, 3-D imaging device, etc., may be coupled to input interface 1014 of embodiments, such as to provide source video herein. Output interface 1015 facilitates coupling one or more output components or devices to processor(s) 1011. For example, a user may be provided output of data, images, video, sound, etc. from electronic device 1010 through one or more output devices (e.g., a display monitor, a touch screen, a printer, a speaker, etc.) coupled to output interface 1015. Output interface 1015 of embodiments may provide an interface to other electronic components, devices and/or systems (e.g., a memory, a video decoder, a radio transmitter, a network interface card, devices such as a computer, a laptop computer, a tablet device, a server, a dedicated spatial processing component or device, a smartphone, a PDA, an IOTA device, a network equipment, a set-top-box, a cable headend system, a smart TV, etc.).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Moreover, the scope of the present application is not intended to be limited to the particular embodiments of the process, machine, manufacture, composition of matter, means, methods and steps described in the specification.

The invention claimed is:

1. A method for treating a subject with minimal residual disease (MRD), the method comprising:

(a) assaying a pre-surgery blood sample, a resected tumor sample, or a biopsy tumor sample of the subject, to detect a set of k truncal mutations;

(b) assaying a plasma cell-free deoxyribonucleic acid (cfDNA) sample obtained or derived from the subject after receiving a surgery, to detect a post-surgery mutation profile for the set of k mutations;

(c) detecting the MRD based at least in part on the post-surgery mutation profile for the set of k truncal mutations, at least in part by:

(i) extracting a set of sequencing reads from the plasma cfDNA sample that align to a genomic position of the set of k truncal mutations, (ii) creating a feature profile for each sequencing read of the set of sequencing reads, (iii) processing the feature profile for each sequencing read of the set of sequencing reads using a trained machine learning classifier, to classify each sequencing read of the set of sequencing reads as either (1) a sequencing read having a true variant or (2) a sequencing read having a sequencing error, (iv) determining an MRD predictive score indicative of a proportion, among the set of sequencing reads aligning to the genomic position of the set of k truncal mutations, that are classified as sequencing reads having true variants, and (v) detecting the MRD based at least in part on the MRD predictive score; and (d) responsive to detecting the MRD, administering cancer therapy to the subject, wherein the cancer therapy comprises chemotherapy, radiation therapy, follow-up surgery, immunotherapy, cell therapy, proton therapy, or a combination thereof.

2. The method of claim 1, wherein determining the MRD predictive score further comprises:

(i) obtaining a set of k randomly sampled sites in a genome that do not include the set of k mutations but comprise matching characteristics of the set of k truncal mutations, wherein the matching characteristics comprise a number of mutations, a distribution of nucleotides, or a depth of coverage, or a combination thereof;

(ii) extracting a second set of sequencing reads from the plasma cfDNA sample that align to a genomic position of the set of k randomly sampled sites;

(iii) processing the second set of sequencing reads using a trained machine learning classifier, to classify each of the second set of sequencing reads as (1) a sequencing read having a true variant or (2) a sequencing read having a sequencing error;

(iv) filtering out sequencing reads having a sequencing error from the second set of sequencing reads, thereby generating a set of filtered sequencing reads; and (v) determining the MRD predictive score based at least in part on the set of filtered sequencing reads.

3. The method of claim 2, wherein (c) further comprises performing a plurality of iterations of (i) to (v) to determine a plurality of MRD predictive scores, and detecting the MRD based at least in part on the plurality of MRD predictive scores.

4. The method of claim 1, wherein (a) further comprises assaying the pre-surgery blood sample of the subject.

5. The method of claim 4, wherein the pre-surgery blood sample comprises a plasma sample.

6. The method of claim 1, wherein (a) further comprises assaying the resected tumor sample of the subject.

7. The method of claim 1, wherein (a) further comprises assaying the biopsy tumor sample of the subject.

8. The method of claim 1, wherein detecting the set of k truncal mutations is further based at least in part on assaying a matched normal sample of the subject.

9. The method of claim 1, wherein detecting the set of k truncal mutations is further based at least in part on assaying a white blood cell DNA sample of the subject.

10. The method of claim 1, wherein the set of k truncal mutations comprises somatic single nucleotide variants (SNVs).

11. The method of claim 1, wherein the feature profile for each sequencing read of the set of sequencing reads comprises a sequencing read alignment quality of the sequencing read, a sequencing quality of individual bases in the sequencing read, a sequencing context of the sequencing read, a PHRED score of the sequencing read, or a paired-end insert size of the sequencing read.

12. The method of claim 1, wherein the cancer therapy comprises the chemotherapy.

13. The method of claim 1, wherein the cancer therapy comprises the radiation therapy.

14. The method of claim 1, wherein the cancer therapy comprises the follow-up surgery.

15. The method of claim 1, wherein the cancer therapy comprises the immunotherapy.

16. The method of claim 1, wherein the cancer therapy comprises the cell therapy.

17. The method of claim 1, wherein the cancer therapy comprises the proton therapy.

* * * * *